US012582301B2

(12) United States Patent
Nielsen et al.

(10) Patent No.: US 12,582,301 B2
(45) Date of Patent: Mar. 24, 2026

(54) MEDICAL VISUALISATION SYSTEM

(71) Applicant: AMBU A/S, Ballerup (DK)

(72) Inventors: Morten Grønning Nielsen, Copenhagen N (DK); Line Sandahl Ubbesen, Holte (DK)

(73) Assignee: AMBU A/S, Ballerup (DK)

( * ) Notice: Subject to any disclaimer, the term of this patent is extended or adjusted under 35 U.S.C. 154(b) by 363 days.

(21) Appl. No.: 18/566,701

(22) PCT Filed: Jun. 13, 2022

(86) PCT No.: PCT/EP2022/066029
§ 371 (c)(1),
(2) Date: Dec. 4, 2023

(87) PCT Pub. No.: WO2022/263377
PCT Pub. Date: Dec. 22, 2022

(65) Prior Publication Data
US 2024/0260822 A1      Aug. 8, 2024

(30) Foreign Application Priority Data

Jun. 15, 2021      (DK) .............................. PA202170303

(51) Int. Cl.
*A61B 1/04* (2006.01)
*A61B 1/00* (2006.01)
(Continued)

(52) U.S. Cl.
CPC ............ *A61B 1/04* (2013.01); *A61B 1/00042* (2022.02); *A61B 1/0005* (2013.01);
(Continued)

(58) Field of Classification Search
CPC ..... A61B 1/04; A61B 1/00042; A61B 1/0005; A61B 1/0052; G06F 3/038;
(Continued)

(56) References Cited

U.S. PATENT DOCUMENTS

| 11,166,622 B2 | 11/2021 | Ubbesen et al. |
| 11,166,624 B2 | 11/2021 | Ubbesen et al. |
(Continued)

FOREIGN PATENT DOCUMENTS

| AU | 2011101195 B4 | 11/2011 | |
| WO | WO-2020230851 A1 * | 11/2020 | ........... G06F 3/0488 |

OTHER PUBLICATIONS

Translation of WO 2020/230851 (Year: 2020).*
(Continued)

*Primary Examiner* — Mark R Gaworecki
(74) *Attorney, Agent, or Firm* — Faegre Drinker Biddle & Reath LLP

(57) ABSTRACT

A monitor device operable to receive image data from a medical visualization device and a medical visualization system comprising the monitor device are disclosed. The monitor device includes a housing and a processing unit adapted to receive the image data from the medical visualization device and cause a display to display a graphical user interface. The monitor device displays a live representation of the image data within a first portion of the graphical user interface and displays a stopwatch button within a second portion of the graphical user interface.

17 Claims, 11 Drawing Sheets

(51) Int. Cl.

| | |
|---|---|
| *A61B 1/005* | (2006.01) |
| *G06F 3/038* | (2013.01) |
| *G06F 3/048* | (2013.01) |
| *G06F 3/04845* | (2022.01) |
| *G06F 3/04847* | (2022.01) |
| *G16H 30/20* | (2018.01) |
| *G16H 30/40* | (2018.01) |
| *G16H 40/63* | (2018.01) |

(52) U.S. Cl.
CPC ............ *A61B 1/0052* (2013.01); *G06F 3/038* (2013.01); *G06F 3/04845* (2013.01); *G06F 3/04847* (2013.01); *G16H 30/20* (2018.01); *G16H 30/40* (2018.01); *G16H 40/63* (2018.01); *G06F 2203/04803* (2013.01)

(58) Field of Classification Search
CPC ............. G06F 3/04845; G06F 3/04847; G06F 2203/04803; G16H 30/20; G16H 30/40; G16H 40/63
See application file for complete search history.

(56) References Cited

U.S. PATENT DOCUMENTS

| | | | |
|---|---|---|---|
| 11,266,297 | B2 | 3/2022 | Ubbesen et al. |
| 11,426,055 | B2 | 8/2022 | Ubbesen |
| 11,707,181 | B2 | 7/2023 | Ubbesen et al. |
| 2010/0064255 | A1 | 3/2010 | Rottler et al. |
| 2018/0325356 | A1 | 11/2018 | Tateshita et al. |
| 2019/0183591 | A1 | 6/2019 | Johnson et al. |
| 2019/0279520 | A1 | 9/2019 | Wilson et al. |
| 2020/0183579 | A1 | 6/2020 | Ive et al. |
| 2021/0200683 | A1 | 7/2021 | Bavishi et al. |

OTHER PUBLICATIONS

"Chron me", URL: https://web.archive.org/web/20201126114756/http:/online-stopwatch.chronme.com/ , Retrieved on Dec. 7, 2022, 1 page.

Examination and Search Report for Denmark Application No. DK PA202170303, mailed on Jan. 28, 2022, 11 pages.

International Search Report and Written Opinion received for PCT Patent Application No. PCT/EP2022/066029, mailed on Oct. 13, 2022, 14 pages.

Stopwatch 2—Advanced lap timer for Android, version X4. [online] [multimedia] Google Play, 7. . . , Retrieved on Dec. 7, 2023, URL: https://play.google.com/store/apps/details?id=uk.co.dedmondson.timer.laptimer, Oct. 29, 2023, 4 pages.

* cited by examiner

MEDICAL VISUALISATION SYSTEM

CROSS REFERENCE TO RELATED APPLICATIONS

This application is a National Phase entry under 35 U.S.C. § 371 of International Application No. PCT/EP2022/066029, filed Jun. 13, 2022, which claims the benefit of and priority from Denmark Patent Application No. PA202170303, filed Jun. 15, 2021; the disclosures of said applications are incorporated by reference herein in their entirety.

TECHNICAL FIELD

The present disclosure relates to a medical visualization system and elements thereof. Particularly, the present disclosure relates to a monitor device for medical visualization devices, such as endoscopes, laryngoscopes etc., in particular to a monitor device comprising a touch sensitive display.

BACKGROUND

A medical visualization device may be utilized to visually examine certain areas of the body of a person, such as inside a body cavity of the person. For example, a medical visualization device may be used to inspect the airways, the digestive tract, or the intestines.

A medical visualization device may be provided with a camera and be attached to a monitor device, such as a monitor with a display screen, a video output from the camera of the visualization device may be received and displayed at the monitor device, thereby allowing an operator to control the visualization device to inspect an area of interest.

For example, a visualization device may be an endoscope, such as a disposable endoscope. An endoscope comprises an operating handle at the proximal end and an insertion cord extending from the handle towards a distal end. The handle is configured to be held by an operator and inter alia comprises externally protruding operating members connected to internal control means allowing the operator to control the movement of a bending section near the distal end of the insertion cord, while advancing the distal end of the insertion cord to a desired location e.g. within a body cavity of a person. By means of an attached monitor device, such as a monitor with a display screen, the location to which the distal end has been advanced may be inspected using the endoscope.

The monitor device of a medical visualization system may be provided with some functionality, such as ability to save still images and/or video sequences of the view from the attached visualization device. Furthermore, the monitor device may comprise some image processing capabilities, and may be configured to output a video or image output, e.g. to an external display.

SUMMARY

It is an object of the present disclosure to provide a solution which at least improve the solutions of the prior art. Particularly, it is an object of the present disclosure to provide a graphical user interface for a medical visualization system which facilitates and enhances human interaction with the system. Particularly, it is an object of the present disclosure to provide solutions which facilitates easy recording of chronological events during a procedure of using the medical visualization system.

The present disclosure relates to a monitor device operable to receive image data from one or more medical visualization devices, and a medical visualization system comprising the monitor device. The present disclosure further relates to a graphical user interface for such monitor device.

Accordingly, a monitor device is disclosed, wherein the monitor device is operable to receive image data from one or more medical visualization devices. The medical visualization devices may be coupled or couplable to the monitor device.

The monitor device comprises a housing, and a processing unit. The processing unit is adapted to receive the image data from the medical visualization device and cause a display, e.g. a touch sensitive display, to display a graphical user interface. The display may be a display of the monitor device, or an external display coupled to the monitor device.

The monitor device displays a live representation of the image data within a first portion of the graphical user interface. The monitor device displays a stopwatch button within a second portion of the graphical user interface. The second portion and the first portion are non-overlapping.

While displaying the live representation of the image data, the monitor device is adapted to detect a first user input corresponding to selection of the stopwatch button. In response to detection of the first user input the monitor device activates a time of a stopwatch and displays a timestamp table within the graphical user interface, such as in the second portion of the graphical user interface.

The timestamp table comprises an add timestamp button. The monitor device is adapted to detect a second user input corresponding to selection of the add timestamp button. In response to detection of the second user input the monitor device stores a first timestamp comprising a first timestamp value corresponding to the time of the stopwatch when detecting the second user input and displays a first timestamp entry in the timestamp table comprising the first timestamp value.

Also, a medical visualization system is disclosed. The medical visualization system comprises the disclosed monitor device. The medical visualization system may comprise a medical visualization device. The medical visualization device comprises: an image sensor adapted to generate image data indicative of a view from the medical visualization device, and a handle having one or more programmable buttons. The medical visualization device may further comprise a light emitter adapted to provide illumination of the view.

By the present disclosure, the operator may easily time certain segments of the procedure, and record timing of these segments, as may be required by some guidelines and/or for assessing performance. Also, the stopwatch function makes it possible for the operator to keep track of how long time the patient has been sedated. The present disclosure further provides an improved way of recording such time, which facilitates an enhanced man-machine interaction to perform this task.

BRIEF DESCRIPTION OF THE FIGURES

Embodiments of the disclosure will be described in more detail in the following with regard to the accompanying figures. The figures show one way of implementing the present disclosure and are not to be construed as being limiting to other possible embodiments falling within the scope of the attached claim set.

DETAILED DESCRIPTION

Figure 1:
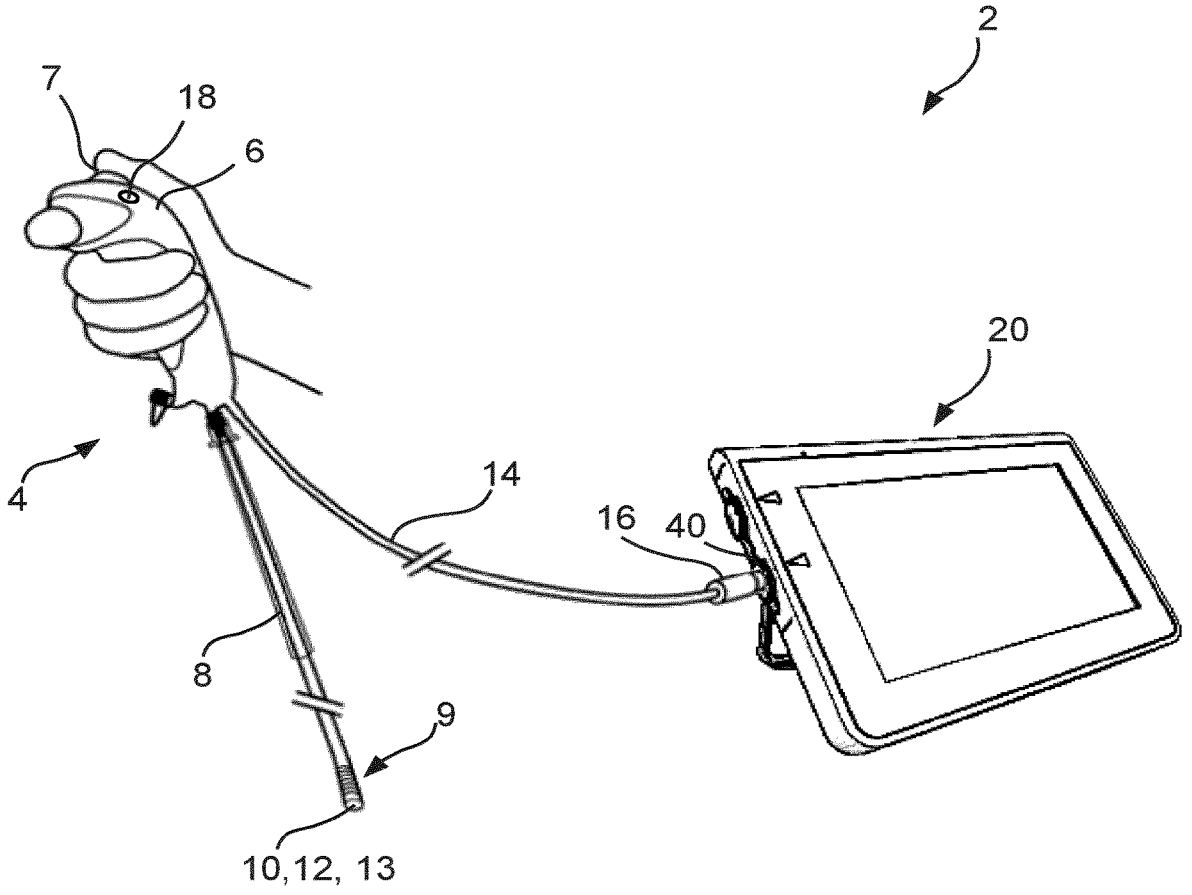
FIG. 1 schematically illustrates an exemplary medical visualisation system.

The medical visualization device may be an endoscope. Particularly, but not exclusively the medical visualization device may be a disposable camera endoscope. Alternatively, the medical visualization device may be a laryngoscope, an endotracheal tube. The medical visualization device may be a disposable, e.g. single use, medical visualization device.

The medical visualization device may comprise an insertion cord extending from the handle to a distal cord portion. The view from the visualization device may be a view from the distal cord portion of the insertion cord.

The handle may comprise a control mechanism adapted to receive an input in a first input direction and/or in a second input direction. The input in the first input direction may cause a bendable section of the insertion cord to bend in a first bending direction. The input in the second input direction may cause the bendable section of the insertion cord to bend in a second bending direction. The second bending direction may be opposite the first bending direction.

The housing of the monitor device may be a first housing and/or a second housing. The first housing may accommodate the display, which may be a touch sensitive display. The second housing may be void of a display.

The first housing may extend in a first direction from a first housing side to a second housing side and in a second direction perpendicular to the first direction from a third housing side to a fourth housing side. The display, such as the touch sensitive display, may be accommodated in the first housing. The display may have a first length in the first direction and a second length in the second direction. The second length may be longer than the first length, e.g. the display may be a 16:9 or 16:10 display. Alternatively, the first length may be longer than the second length, or the first length and the second length may be substantially the same. The touch sensitive display may be any suitable type of touch display, e.g. capacitive touch display or resistive touch display.

The monitor device may comprise one or more connection ports configured to receive a connector of the visualisation device. The connection ports and the corresponding connector of the visualisation device may be a proprietary plug and socket connectors, or any standard connector capable of transmitting therethrough at least the image data from the image sensor. Furthermore, the connector and connection ports may be configured to supply power to the components of the visualisation device.

The one or more connection ports may be arranged on the first housing. The one or more connection ports may be provided on the third housing side, and/or on the fourth housing side. Alternatively or additionally, the one or more connection ports may be arranged on the second housing.

The monitor device may comprise an on/off button. The on/off button may be arranged on the first housing and/or on the second housing. The on/off button may be provided on the third housing side or on the fourth housing side of the first housing. The one or more connection ports may be provided on the third housing side and the on/off button may be provided on the fourth housing side of the first housing.

The monitor device may establish connection to a medical visualisation device. Establishing connection to the medical visualisation device may include receiving a device connector of the respective visualisation device in a connection port of the one or more connection ports of the monitor device. Establishing connection to a medical visualisation device may include obtaining device identifier information from a device identifier (e.g. EPROM, QR-code, NFC, RFID or similar) of the medical visualisation device. For example, establishing connection to a first medical visualisation device may include obtaining first device identifier information from a first device identifier of the first medical visualisation device and/or establishing connection to a second medical visualisation device may include obtaining second device identifier information from a second device identifier of the second medical visualisation device.

The monitor device may comprise a processing unit and memory. The processing unit and/or the memory may be accommodated in the first housing or in the second housing. In some examples, the processing unit and/or the memory may be accommodated in the second housing and the display may be accommodated in the first housing.

The monitor device may comprise an orientation sensor, e.g. for determining the orientation of the monitor device, such as of the first housing, relative to gravity. The orientation sensor may comprise one or more accelerometers and/or a gyroscope. The orientation sensor may be accommodated in the first housing. The processing unit may be connected to the orientation sensor to receive an orientation signal indicative of the orientation of the monitor device, such as of the first housing of the monitor device.

The processing unit may be connected to the display to control display of information with the display. The processing unit may be adapted to receive a signal from the display, particularly when the display is a touch sensitive display, indicative of touch inputs on the display. Thereby, the monitor device may detect user inputs, e.g. in the form of touch inputs, with the touch sensitive display. Alternatively, the monitor device may detect user inputs by means of a keyboard, a trackpad, a mouse etc. Touch inputs may, for example, comprise single tap(s), double tap(s), or swipe(s) on the touch sensitive display.

The processing unit may be connected to the memory and be adapted to read and write data from and to the memory.

In the present disclosure, processes of the monitor device, such as displaying, processing, evaluating, registering, receiving, storing, activating, deactivating etc., may be performed by the processing unit of the monitor device. For example, when in the following, it is mentioned that the monitor device may display content, this may be performed by the processing unit causing a display, e.g. of the monitor device or an external display, to display the content.

The monitor device may comprise a power unit for powering the monitor device. The power unit may comprise a rechargeable battery and/or a power connection for connecting the power unit to an external power supply, such as a conventional AC power socket. The power unit may be accommodated in the first housing. Alternatively, the power unit may be accommodated in the second housing.

The monitor device may comprise the graphical user interface. The monitor device and/or the processing unit of the monitor device may display with the display the graphical user interface. The graphical user interface may comprise one or more portions, such as a plurality of portions, e.g. including the first portion and the second portion, and optionally a third portion and/or a fourth portion. The portions may be non-overlapping portions, such as a plurality of non-overlapping portions. Each of the plurality of portions may extend substantially throughout the first length in the first direction. The first portion may be arranged between the third portion and the second portion along the second direction. The second portion may be arranged between the fourth portion and the first portion along the second direction. The fourth portion may be arranged between a side of the first housing, e.g. the third housing side, and the second portion along the second direction. The third portion may be arranged between another side of the first housing, e.g. the fourth housing side, and the first portion along the second direction. The first portion and the second portion may be arranged between the third portion and the fourth portion along the second direction. The first portion of the graphical user interface may be square. The first portion of the graphical user interface may occupy the centre of the display. The first portion of the graphical user interface may be larger along the second direction than the second portion, the third portion and/or the fourth portion, individually and/or collectively. The first portion of the graphical user interface may extend throughout more than 40% of the second length in the second direction, such as more than 50% of the second length in the second direction, such as more than 60% of the second length in the second direction.

The medical visualization device may, as stated previously, comprise a control mechanism adapted to receive an input in a first input direction and/or in a second input direction, and wherein the input in the first input direction may cause a bendable section of the insertion cord to bend in a first bending direction, and wherein the input in the second input direction may cause the bendable section to bend in a second bending direction. The live representation of the image data may have directions corresponding to directions of the image sensor generating the image data. The first bending direction may correspond to a first image direction of a representation of the image data, such as the live representation of the image data. The second bending direction may correspond to a second image direction of the representation of the image data, such as the live representation of the image data. The first image direction and/or the second image direction may be parallel to the first direction of the first housing.

The monitor device displays a live representation of the image data within the first portion of the graphical user interface. The monitor device displays a stopwatch button within the second portion of the graphical user interface. While displaying the live representation of the image data, the monitor device is adapted to detect a first user input corresponding to selection of the stopwatch button.

In response to detection of the first user input corresponding to selection of the stopwatch button the monitor device activates a time of a stopwatch and displays a timestamp table within the graphical user interface, such as in the second portion of the graphical user interface.

The handle of the medical visualization device may comprise one or more buttons operable to receive one or more button inputs, e.g. a first button input and/or a second button input. The medical visualization device may be operable to transmit a button signal indicative of a respective button input to the monitor device. For example, the medical visualization device may be operable to transmit a first button signal indicative of the first button input and/or to transmit a second button signal indicative of the second button input to the monitor device.

Any user inputs described in the following may be touch inputs on the display, which may be a touch sensitive display. However, alternatively or additionally, a button signal indicative of a button input of the one or more buttons of the handle may be equivalent to such user input.

For example, the first user input may correspond to a first button input of the one or more buttons of the handle. Hence, in response to receipt of the first button signal the monitor device may activate the time of the stopwatch and display the timestamp table.

"Activating" the time of the stopwatch may refer to starting of the time, e.g. starting from 00:00, or resuming the time, e.g. continuing after having previously being paused. Hence, when the time of the stopwatch is active it refers to the time counting upwards. Conversely, "deactivating" the time of the stopwatch may refer to pausing or stopping the time, after which the time may again be activated. Hence, when the time of the stopwatch is deactivated, it refers to the time not increasing.

The timestamp table comprises an add timestamp button. The monitor device is adapted to detect a second user input corresponding to selection of the add timestamp button.

In response to detection of the second user input corresponding to selection of the add timestamp button the monitor device stores a first timestamp comprising a first timestamp value corresponding to the time of the stopwatch when detecting the second user input and displays a first timestamp entry in the timestamp table comprising the first timestamp value.

The second user input may be a touch input on the display, which may be a touch sensitive display. Alternatively or additionally, the second user input may correspond to a second button input of the one or more buttons of the handle. Hence, for example, in response to receipt of the second button signal the monitor device may store a primary timestamp, e.g. the first timestamp or another timestamp, comprising a primary timestamp value, e.g. the first timestamp value or a different timestamp value, corresponding to the value of the time of the stopwatch when receiving the second button signal. The monitor device may, e.g. in response to receipt of the second button signal, display a primary timestamp entry in the timestamp table comprising the primary timestamp value.

The first button input and the second button input may be different inputs, e.g. of the same button, e.g. a short press and a long press. Alternatively or additionally, the first button input and the second button input may be inputs of different buttons, e.g. of a first button and a second button, respectively.

While the time of the stopwatch is active, the monitor device may be adapted to detect a third user input corresponding to selection of the stopwatch button. In response to detection of the third user input the monitor device may deactivate, such as pausing or stopping, the time of the stopwatch.

The stopwatch button, e.g. prior to detection of the first user input, may be displayed in a first visual mode. The stopwatch button may be displayed in the first visual mode in accordance with the time of the stopwatch being deactivated and/or not yet activated. In response to detection of the first user input the monitor device may update the stopwatch button to be in a second visual mode. The stopwatch button may be displayed in the second visual mode in accordance with the time of the stopwatch being active. In response to detection of the third user input the monitor device may update the stopwatch button to be in the first visual mode. Thereby, the stopwatch button may signal to the user whether the time of the stopwatch is active or deactivated and may further provide feedback to the operator that the user input is indeed received. The first visual mode may include the stopwatch button comprising a first color, e.g. white. The second visual mode may include the stopwatch button comprising a second color, e.g. different than the first color, e.g. green.

The stopwatch button may comprise a time indicator. The time indicator may visually indicate the time of the stopwatch. While the time of the stopwatch is active, the monitor device may be adapted to recurrently update the time indicator to indicate the time of the stopwatch. Thereby, the stopwatch button may provide information to the operator of the total time of the stopwatch, while simultaneously signaling to the user whether the time of the stopwatch is active or deactivated.

The timestamp table may comprise a plurality of time-stamp entries, e.g. resulting from a plurality of user inputs corresponding to selection of the add timestamp button.

The monitor device may store a timestamp comprising a timestamp value corresponding to the time of the stopwatch when detecting a user input corresponding to selection of the add timestamp button. A corresponding timestamp entry may be displayed in the timestamp table comprising the corresponding timestamp value.

For example, the monitor device may store a second timestamp comprising a second timestamp value corresponding to the time of the stopwatch when detecting a user input (e.g. before the second user input) corresponding to selection of the add timestamp button. A second timestamp entry may be displayed in the timestamp table comprising the second timestamp value.

The monitor device may store one or more third time-stamps comprising respective one or more third timestamp values corresponding to respective times of the stopwatch when detecting respective user inputs (e.g. before the second user input) corresponding to selection of the add timestamp button. One or more third timestamp entries may be displayed in the timestamp table comprising the respective one or more third timestamp values. The one or more third timestamp values may be between the second timestamp value and the first timestamp value.

Each of the timestamps may comprise a timestamp name. For example, the first timestamp may comprise a first timestamp name, the second timestamp may comprise a second timestamp name, and/or the one or more third timestamps may comprise respective one or more third timestamp names. The first timestamp entry in the time-stamp table may comprise the first timestamp name. The second timestamp entry in the timestamp table may comprise the second timestamp name. The one or more third timestamp entries in the timestamp table may comprise the respective one or more third timestamp names.

The monitor device may be adapted to detect a user input corresponding to selection of a timestamp entry in the timestamp table. In response to detection of the user input corresponding to selection of the timestamp entry, the monitor device may open a dialogue enabling editing of the timestamp name of the timestamp entry. For example, the monitor device may be adapted to detect a fourth user input corresponding to selection of the first timestamp entry in the timestamp table. In response to detection of the fourth user input the monitor device may open a dialogue enabling editing of the first timestamp name. Thereby, the operator may be able to rename the timestamps to reflect what occurred at the time of the timestamp.

Each of the timestamp entries may comprise a difference value corresponding to a time difference between the time-stamp value and a preceding timestamp value of an immediately preceding timestamp entry. For example, the first timestamp entry in the timestamp table may comprise a first difference value corresponding to a time difference between the first timestamp value and a preceding timestamp value of an immediately preceding timestamp entry, e.g. the second timestamp value or one of the one or more third timestamp values.

The timestamp table may comprise an indication of elapsed time since a newest timestamp value. For example, after storing the first timestamp and displaying the first timestamp entry in the timestamp table, the timestamp table may comprise an indication of elapsed time since the first timestamp value. Thereby, the operator is made aware of the time elapsed since the latest timestamp, which may be relevant, for example, when the previous time stamp indicates administration of sedatives, which works for a certain period of time.

After detection of the second user input, the timestamp table may comprise a plurality of timestamp entries, e.g. including the first timestamp entry and the second timestamp entry. The second timestamp entry may comprise a second timestamp value being before the first timestamp value. The second timestamp entry may be displayed above the first timestamp entry in the timestamp table. One or more third timestamp entries may be displayed between the first time-stamp entry and the second timestamp entry in the time-stamp table.

A threshold number of timestamp entries to display in the second portion of the graphical user interface may be provided, e.g. such as to account for the operator storing more timestamps than the size of the second portion permits display of, when observing readability of the timestamp table. In some examples, the number of the plurality of timestamp entries may be more than a threshold number of timestamp entries to display in the second portion of the graphical user interface. The threshold number of timestamp entries may be based on the first length of the display in the first direction. The second timestamp entry, e.g. being close to the top of the second portion of the graphical user interface, may be displayed with fading visibility from bottom to top of the second timestamp entry. Thereby, the monitor device signals to the user that there are more timestamp than what is currently displayed. When the number of the plurality of timestamp entries are more than the threshold number, the timestamp table may be scrollable, e.g. by detection of a swipe input, such as swipe up and/or swipe down.

The monitor device may be adapted to detect disconnection of a visualization device. In response to disconnection of the medical visualization device from the monitor device, e.g. in response to detection of disconnection of the medical visualization device from the monitor device, the monitor device displays a procedure overview. The procedure overview comprises a second timestamp table. The second timestamp table may comprise the first timestamp entry. The second timestamp table may comprise each timestamp entry including the first timestamp entry. The second timestamp table may comprise the second timestamp entry and/or the one or more third timestamp entries. The procedure overview may be displayed within the first portion of the graphical user interface and/or overlaying the first portion of the graphical user interface. The procedure overview may extend into the second portion and/or the third portion of the graphical user interface.

The monitor device may be adapted to detect reconnection of the medical visualization device, e.g. the monitor device may, e.g. by obtaining device identifier information from a device identifier of the medical visualization device, detect that a connected medical visualization device corresponds to a previously disconnected visualization device.

In response to reconnection of the medical visualization device to the monitor device, e.g. in response to detection of reconnection of the medical visualization device to the monitor device, the monitor device may hide the procedure overview and display the live representation of the image data within the first portion of the graphical user interface. In response to reconnection of the medical visualization device, the medical visualization device may display the stopwatch button within the second portion of the graphical user interface.

In accordance with the medical visualization device being reconnected within a threshold amount of time after disconnection of the medical visualization device, e.g. within 60 seconds, the monitor device may, in response to detection of a fifth user input corresponding to selection of the stopwatch button, deactivate or resume the time of the stopwatch. For example, the time of the stopwatch may be deactivated in case it is active or may be resumed if it was deactivated prior to disconnection of the medical visualization device.

In accordance with the medical visualization device being reconnected after the threshold amount of time after disconnection of the medical visualization device, e.g. after 60 seconds, the monitor device may, in response to detection of the fifth user input corresponding to selection of the stopwatch button, activate a new time of a new stopwatch.

Thus, in other words, the time of the stopwatch may be continued if the medical visualization device is reconnected within the threshold amount of time, while a new time of a new stopwatch may be initiated if reconnection is performed after the threshold amount of time. By applying a threshold of time where the time of the stopwatch may be continued, the operator is able to continue the procedure in case the medical visualization device was disconnected unintentionally.

The procedure overview may comprise a continue button. The monitor device may, e.g. in accordance with connection of a new medical visualization device to the monitor device and/or in accordance with reconnection of the previous medical visualization device after the threshold amount of time, be adapted to detect a sixth user input corresponding to selection of the continue button. In response to detection of the sixth user input, the monitor device may hide the procedure overview, and display the live representation of the image data within the first portion of the graphical user interface. In response to detection of the sixth user input, the monitor device may display the stopwatch button within the second portion of the graphical user interface. In response to detection of a seventh user input corresponding to selection of the stopwatch button, the monitor device may deactivate or resume the time of the stopwatch. For example, the time of the stopwatch may be deactivated in case it is active or may be resumed if it was deactivated prior to disconnection of the medical visualization device.

Thus, in other words, the time of the stopwatch may be continued with a new medical visualization device, e.g. if the operator requires a different type of medical visualization device for the procedure, or with the same medical visualization device, by providing a user input corresponding to selection of the continue button of the procedure overview.

The monitor device may display one or more actionable items within the third portion of the graphical user interface. The one or more actionable items may comprise an image capture button and/or a video capture button. In response to a user input corresponding to selection of the image capture button, an image data file corresponding to the image data received when the user input corresponding to the image capture button was detected may be stored, e.g. in memory of the monitor device. In response to a user input corresponding to selection of the video capture button, a video sequence of image data corresponding to the image data received when the user input corresponding to the video capture button was detected may be stored, e.g. in memory of the monitor device. A primary user input corresponding to selection of the video capture button may start collection of image data for the video sequence, and a secondary user input corresponding to selection of the video capture button (subsequent to the primary user input corresponding to selection of the video capture button) may stop the collection of image data for the video sequence. The stored video sequence may correspond to the image data received between the primary and secondary user inputs corresponding to selection of the video capture button.

The monitor device may display a folder icon, e.g. within the second portion of the graphical user interface, may be displayed, e.g. by the monitor device and/or with the touch sensitive display of the monitor device. The folder icon may comprise a visual representation of a count of stored files stored during the procedure session.

The monitor device may be adapted to receive and/or detect an eighth user input corresponding to selection of the image capture button of the one or more actionable items, e.g. while displaying the live representation within the first portion of the graphical user interface and/or while displaying the timestamp table in the second portion of the graphical user interface.

In response to detection of the eighth user input, the monitor device may store a first image file corresponding to the image data received when the eighth user input was detected. The monitor device may further, in response to the eighth user input, associate the first image file with a procedure session. For example, the monitor device may position the first image file in a folder of the procedure session. The procedure session may correspond to the connected visualization device.

Also in response to detection of the eighth user input a first representation of a still image corresponding to the stored first image file may be displayed, e.g. within the second portion of the graphical user interface. Providing a representation of the captured still image notifies the operator that an image is stored and provides an example of the stored image allowing the operator to quickly confirm that the image shows what he/she intended to capture. The timestamp table may be hidden when displaying the first representation.

After a predetermined delay after detection of the eighth user input an animation of transitioning the first representation to the folder icon may be displayed. Thereby, the operator may be visually notified that the captured image is stored and placed in the folder represented by the folder icon. Thus, the operator is made aware where he/she is able to retrieve the just captured image.

Preferable the predetermined delay is between 1-8 seconds, such as between 3-7 seconds, such as between 4-6 seconds, such as 5 seconds or between 1.5-3 seconds, such as 1.5 seconds or such as 2 seconds. The animation preferably may have a duration between 100-1500 ms, such as between 300-1000 ms, such as between 300-800 ms, such as between 300-600 ms or between 500-700 ms. For example, the duration of the animation may be 400 ms, 500 ms or 600 ms. The duration of the animation may be a fraction of the predetermined delay, such as between $\frac{1}{7}$ to $\frac{1}{13}$ of the predetermined delay, such as between $\frac{1}{8}$-$\frac{1}{12}$ of the predetermined delay, such as between $\frac{1}{9}$-$\frac{1}{11}$ of the predetermined delay, such as $\frac{1}{10}$ of the predetermined delay.

After displaying the animation, the monitor device may display the timestamp table in the second portion of the graphical user interface. Hence, after having displayed the first representation and the animation, during which the timestamp table may have been hidden, the monitor device may (re)display the timestamp table in the second portion of the graphical user interface.

The monitor device may display a timeline, e.g. as part of the procedure overview, instead of the procedure overview, or following the procedure overview. The timeline may extend from a first position to a second position. The timeline may comprise one or more marks between the first position and the second position. Each or the one or more marks may be indicative of a timestamp, such as the first timestamp, the second timestamp and/or the one or more third timestamps, or a captured image or video sequence. The one or more marks may be chronologically ordered along the timeline. The timeline may provide the operator with a chronological overview of the timestamps, images and/or videos, stored during the procedure.

The monitor device may display one or more actionable menu items within the fourth portion of the graphical user interface. The actionable menu items may comprise one or more of a login menu item for initiating a login procedure, a settings menu item for accessing a settings menu, an archive menu item for browsing an archive, and/or a default menu item for returning to a default view.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

FIG. 1 schematically illustrates an exemplary medical visualization system 2 comprising a medical visualization device 4 and a monitor device 20. The visualization device 4 has an image sensor 12, e.g. a CCD or a CMOS, configured to generate image data indicative of a view from the visualization device 4. In the illustrated example, the visualization device 4 is an endoscope comprising a handle 6 and an insertion cord 8, extending from the handle 6 to a distal cord portion 10. The image sensor 12 may be configured to generate image data indicative of a view from the distal cord portion 10 of the insertion cord 8. The visualization device 4 may further comprise a light emitter 13 adapted to provide illumination of the view. The light emitter may be an LED, an optical fiber connectable to a light source, or similar element known to provide illumination.

The visualization device 4 may be connected to the monitor device 20. In the illustrated example, a device cable 14 extending from the handle 6 terminates in a device connector 16 connected to a connection port 40 of the monitor device 20. The monitor device 20 is operable to receive image data generated by the image sensor 12 of the visualization device 4. For example, the monitor device 20 may receive image data generated by the image sensor 12 via the device cable 14, the connector 16 and connection port 40. Alternatively, the visualization device 4 may be wirelessly connected to the monitor device 20.

The handle 6 comprises a control mechanism 7 adapted to receive an input in a first input direction and/or in a second input direction. The touch input in the first input direction on the control mechanism 7 causes a bending section 9 of the insertion cord 8 to bend in a first bending direction, e.g. via wires extending from the handle, through the insertion cord 8 to the bending section 9. The touch input in the second input direction on the control mechanism 7 causes the bending section 9 of the insertion cord 8 to bend in a second bending direction. The first input direction and the second input direction may be opposite. The first bending direction and the second bending direction may be opposite. Bending the bending section 9 of the insertion cord 8 may cause a movement of the distal end 10 and the image sensor 12 in a direction relative to the image sensor 12. Thereby, seeing an image generated by the image sensor 12, a direction, e.g. up or down, in the image may correspond to a respective input on the control mechanism 7.

The handle 6 may have one or more buttons 18. The button(s) 18 may be configured to execute functions of the monitor device, such as capturing of images, start/stop of video recordings, changing image characteristics, functions of a stopwatch etc. By having one or more buttons 18 on the handle 6, the operator may easily execute desired functionality without having to reach over to tap a button on the monitor device 20.

The one or more buttons 18 may be operable to receive one or more button inputs, e.g. including a first button input and a second button input. One button may be operable to receive a plurality of button inputs, e.g. a long press and a short press. The medical visualization device 4 may be operable to transmit a button signal indicative of a corresponding button input. In some examples, the monitor device 2 may be programmed to assign desired functionality to a button signal. Thus, any user inputs described in the following may be touch inputs on the display 26, which may be a touch sensitive display, but alternatively or additionally, a button signal indicative of a button input of the one or more buttons 18 may be equivalent to such user input.

Figures 2, 3:
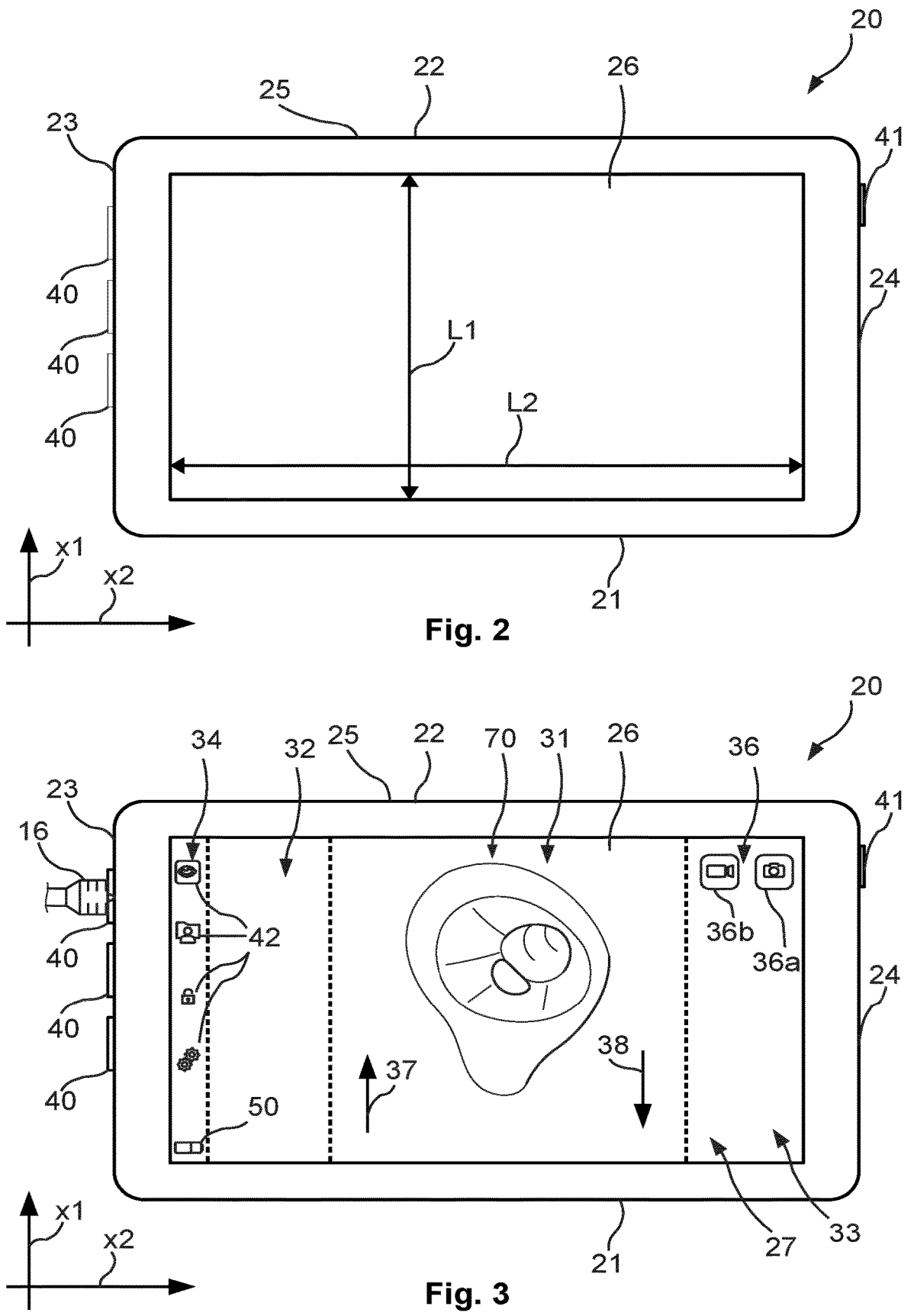
FIG. 2 schematically illustrates an exemplary monitor device.
FIG. 3 schematically illustrates an exemplary monitor device.

FIG. 2 schematically illustrates an exemplary monitor device 20, such as the monitor device 20 as illustrated in FIG. 1. The monitor device 20 comprises a first housing 25. The first housing 25 extends in a first direction x1 from a first housing side 21 to a second housing side 22 and in a second direction x2 perpendicular to the first direction x1 from a third housing side 23 to a fourth housing side 24. The monitor device comprises a touch sensitive display 26 accommodated in the first housing 25. The touch sensitive display 26 has a first length L1 in the first direction x1 and a second length L2 in the second direction x2. The second length L2 may be longer than the first length L1 as illustrated. In some examples, the monitor device 20 may comprise a second housing (not shown), which does not comprise a display. For example, the second housing may be coupled to the first housing 25, or the second housing may be coupled to an external display.

The monitor device 20 may comprise one or more connection port(s) 40, such as three connection ports 40, as illustrated. The connection ports 40 may allow visualization devices to be connected. The connection port(s) 40 may be arranged at the third housing side 23, as illustrated. Alternatively or additionally, connection port(s) 40 may be arranged at the fourth housing side 24. In some examples, the monitor device 20 may provide for wireless connection with the visualization devices, in which case the connection ports 40 may be omitted. However, in some examples, the monitor device 20 may comprise both connection ports 40 and the ability to wireless connect to visualization devices.

The monitor device may comprise an on/off button 41, which may be provided on the fourth housing side 24, as illustrated.

FIG. 3 schematically illustrates an exemplary monitor device 20, such as the monitor device 20 as illustrated in FIGS. 1-2. As illustrated a device connector 16 may be connected to a connection port 40.

The monitor device 20 may be provided with a graphical user interface 27. The graphical user interface 27 may be displayed with the touch sensitive display 26, and the user may interact with the graphical user interface 27, e.g. by means of providing touch inputs on the touch sensitive display 26. In some examples, the monitor device may be provided without a touch sensitive display, and the user may interact with the graphical user interface by other means, e.g. by a keyboard, a trackpad or a mouse.

The graphical user interface 27 comprises a plurality of non-overlapping portions 31, 32, 33, 34. Each of the portions 31, 32, 33, 34 extends substantially throughout the first length L1 in the first direction x1. The non-overlapping portions includes a first portion 31, a second portion 32, a third portion 33 and a fourth portion 34. The first portion 31 is arranged between the third portion 33 and the second portion 32 along the second direction x2. The second portion 32 is arranged between the fourth portion 34 and the first portion 31 along the second direction x2. The fourth portion 34 is arranged between a side of the first housing, e.g. the third housing side 23, and the second portion 32 along the second direction x2. The third portion 33 is arranged between another side of the first housing 25, e.g. the fourth housing side 24, and the first portion 31 along the second direction x2. The first portion 31 and the second portion 32 are arranged between the third portion 33 and the fourth portion 34 along the second direction x2.

The monitor device 20 displays a live representation 70 of the image data within the first portion 31 of the touch sensitive display 26. The first bending direction and the second bending direction of the bending section 9 of the insertion cord 8, as described with respect to FIG. 1, may corresponds to a first image direction 37 and a second image direction 38 of the live representation 70, respectively. The first image direction 37 and the second image direction 38 may be parallel to the first direction x1, as illustrated. The first image direction 37 and the second image direction 38 may be opposite, as illustrated. Thereby, a user operating the control mechanism 7 of visualization device 4 may cause movement of the bending section 9 of the insertion cord 8 to bend in a direction corresponding to the first image direction 37 or the second image direction 38 of the live representation 70.

The monitor device 20 displays with the touch sensitive display 26 one or more actionable items 36 within the third portion 33 of the graphical user interface 27. The actionable items 36 may comprise an image capture button 36a, e.g. for storing an image data file corresponding to the image data received when the image capture button 36a was activated. Alternatively or additionally, the actionable items 36 may comprise a video capture button 36b, e.g. for storing a video sequence of image data corresponding to the image data received when the video capture button 36b was activated.

The monitor device 20 displays with the touch sensitive display 26 one or more actionable menu items 42 within the fourth portion 34 of the graphical user interface 27. The actionable menu items 42 may, for example, comprise a login menu item for initiating a login procedure, a settings menu item for accessing a settings menu, an archive menu item for browsing an archive, and a default menu item for returning to a default view. Also, a battery indicator 50 is displayed in the fourth portion 34.

Figure 4:
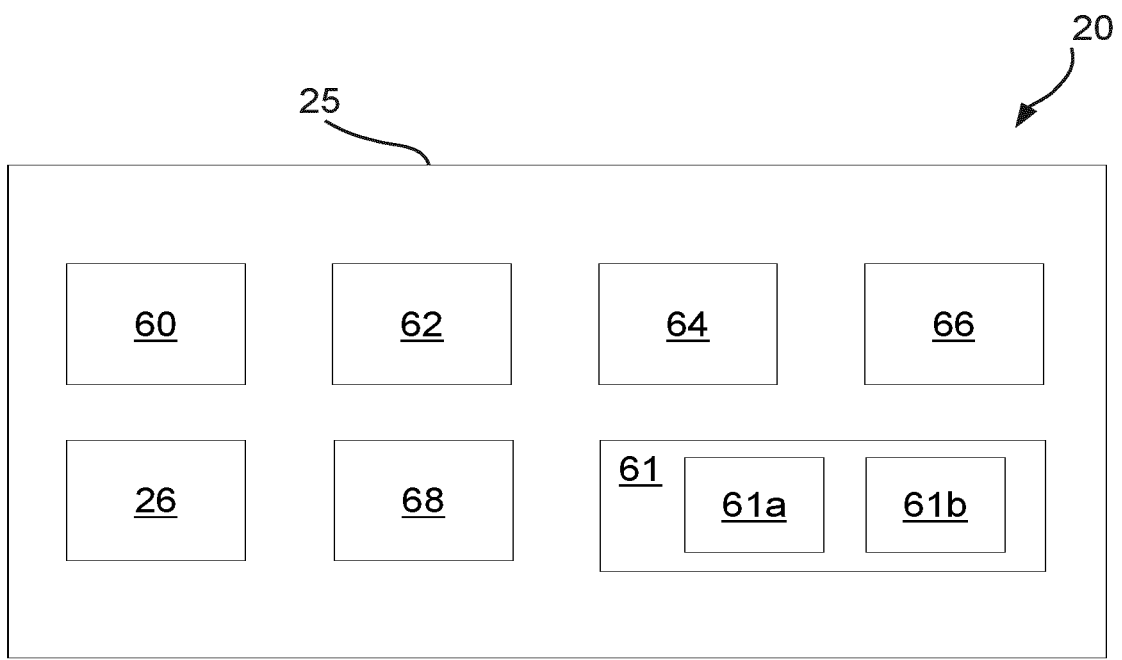
FIG. 4 is a block diagram of an exemplary monitor device.

FIG. 4 is a block diagram of an exemplary monitor device 20, such as the monitor device 20 of the previous figures. The monitor device 20 comprises a processing unit 60 and memory 62. The memory 62 may comprise both volatile and non-volatile memory. The monitor device 20 also comprise an orientation sensor 64 for determining the orientation of a housing, such as the first housing 25, relative to gravity. The orientation sensor 64 may comprise one or more accelerometers and/or a gyroscope. The monitor device 20 comprises input/output module 66, such as for receiving image data from the image sensor 12 via connectors of the visualization device 4. The input/output module 66 may also comprise ethernet connector, Wi-Fi transceiver, Bluetooth transceiver, video connectors, USB ports etc., and respective controllers. The monitor device 20 also comprises the touch sensitive display 26 as described earlier. The monitor device 20 may display information, graphical user interface objects, images, buttons etc., with the touch sensitive display 27. The monitor device 20 also comprises a microphone 68. The monitor device 20 comprises a power unit 61 for powering the monitor device 20. The power unit 61 may comprise a rechargeable battery 61a. The power unit 61 may comprise a power connection 61b for connecting the power unit 61 to an external power supply, such as a conventional AC power socket. The components of the monitor device 20 may be interconnected by buses or signal lines. Some or all of the components of the monitor device may be accommodated in the first housing 25 as illustrated. However, alternatively some of the components, e.g. the processing unit 60, the memory 62, input/output module 66 and/or the power unit 61 may be accommodated in a second housing (not shown) of the monitor device 20.

The power unit 61 may comprise components for, e.g. indirectly measuring, capacity of the rechargeable battery 61a. For example, the power unit 61 may comprise a voltage gauge to measure the voltage of the rechargeable battery 61a. Based on the measured voltage, the remaining capacity of the rechargeable battery 61a may be estimated, e.g. by the processing unit 60. The power unit 61 may also comprise components for measuring power consumption of the monitor device 20. For example, the power unit 61 may comprise a power meter to measure the rate at which the monitor device 20 consumes power from the rechargeable battery 61*a*. The voltage gauge may be a low current consumption integrated circuit, or a resistor coupled in parallel with the battery. A current sensor may be provided, and the power may be computed as the product of the voltage and current. Additionally, an integrated circuit may be provided that includes a voltage gauge and a current sensor, and which outputs a power value in digital form.

The monitor device 20 may display content with the touch sensitive display 26 and/or with an externally coupled display. For example, the monitor device 20 may display content by the processing unit 60 transmitting instructions to the touch sensitive display 26 and/or the externally coupled display indicative of the content to be displayed. The processing unit 60 may be adapted to receive the image data from the visualization device. The processing unit 60 may be adapted to cause a display, such as the touch sensitive display 26 and/or the externally coupled display, to display a live representation of the image data.

The monitor device 20 may receive user input with the touch sensitive display 26. Particularly, the monitor device 20 may detect user inputs with the touch sensitive display 26. For example, a user providing a touch input on the touch sensitive display 26 causes a change in one or more electrical parameters of the touch sensitive display 26 indicative of at least the location of the touch input. Information of the touch input is transmitted from the touch sensitive display 26 to the processing unit 60, and the processing unit 60 may determine whether the touch input corresponds to an action to perform, e.g. whether the location of the touch input corresponds to the location of a soft-button displayed at the touch sensitive display. Alternatively or additionally, the monitor device 20 may receive user inputs by other means, e.g. by a keyboard, a trackpad or a mouse, which may be coupled to the monitor device 20. The monitor device 20 may also or alternatively receive user input by means of buttons on a coupled visualization device.

The user may interact with the monitor device 20 via the graphical user interface 27 by providing user inputs, e.g. by means of providing touch inputs on the touch sensitive display 26, and the monitor device 20 may detect such user inputs with the touch sensitive display 26. A touch input, e.g. a single tap, long press, double tap, swipe or similar, and the location of the touch input on the touch sensitive display 26 is registered by the touch sensitive display 26, which transmits information of the touch input (e.g. including type of touch (double tap, long press, single tap, swipe, etc.) and/or location of the touch) to the processing unit 60 of the monitor device 20. The processing unit 60 interprets the information received and determines whether the touch input corresponds to activation of an action, e.g. whether the touch input correspond to activation of a button displayed with the touch sensitive display 27 at the location of the touch input. In response to a determination that the touch input corresponds to activation of an action, the processing unit 60 performs the respective action.

For example, with reference to FIGS. 3 and 4, to capture an image corresponding to the presently shown live representation 70, e.g. corresponding to the image data received from the image sensor, the user may tap the image capture button 36*a*. The tap and the location of the tap is registered by the touch sensitive display 26, which transmits the information of the tap to the processing unit 60 of the monitor device 20. The processing unit 60 interprets the information received and determines that the user tapped the location corresponding to the image capture button 36*a*. In response thereto, the processing unit 60 stores, in memory 62 an image data file corresponding to the image data received.

In further reference to FIGS. 3 and 4, to capture a video sequence corresponding to the shown live representation 70 over a period of time, e.g. corresponding to the image data received from the image sensor over a period of time, the user may tap the video capture button 36*b*. The tap and the location of the tap is registered by the touch sensitive display 26, which transmits the information of the tap to a processing unit 60 (see FIG. 4) of the monitor device 20. The processing unit 60 interprets the information received and determines that the user tapped the location corresponding to the video capture button 36*b*. In response thereto, the processing unit 60 starts collection of image data received from the image sensor 12 and temporarily stores the data in memory 62. To stop the recording, the user may tap the video capture button 36*b* again. The processing unit 60 determines, based on the signal received from the touch sensitive display 26, that that the user tapped the video capture button 36*b* and stops collecting image data received from the image sensor 12. The processing unit 60 read the temporarily stored data from the memory 62 and create a complete video sequence based thereon, which the processing unit 60 stores in the memory 62.

In the present disclosure, processes of the monitor device 20 is described. It will be understood that in some examples, such processes, such as but not necessarily limited to displaying, processing, evaluating, registering, receiving, storing etc., may be performed by the processing unit 60 of the monitor device 20. However, in some examples, such processes or parts thereof may be performed by other entities, such as cloud computing devices, or other processing means known in the art.

FIGS. 5A-5F schematically illustrates exemplary user interactions with an exemplary graphical user interface 27 of a monitor device 20, such as the monitor device 20 and the graphical user interface 27, as described previously. Particularly, FIGS. 5A-5F schematically illustrates an exemplary functionality of the graphical user interface 27 for using a stopwatch and capturing time stamps during a medical procedure.

The stopwatch function helps the operator to time certain segments of the procedure, and to log timing of these segments, as may be required by some guidelines and/or for assessing performance. Also, the stopwatch function makes it possible for the operator to keep track of how long time the patient has been sedated.

Figure 5A:
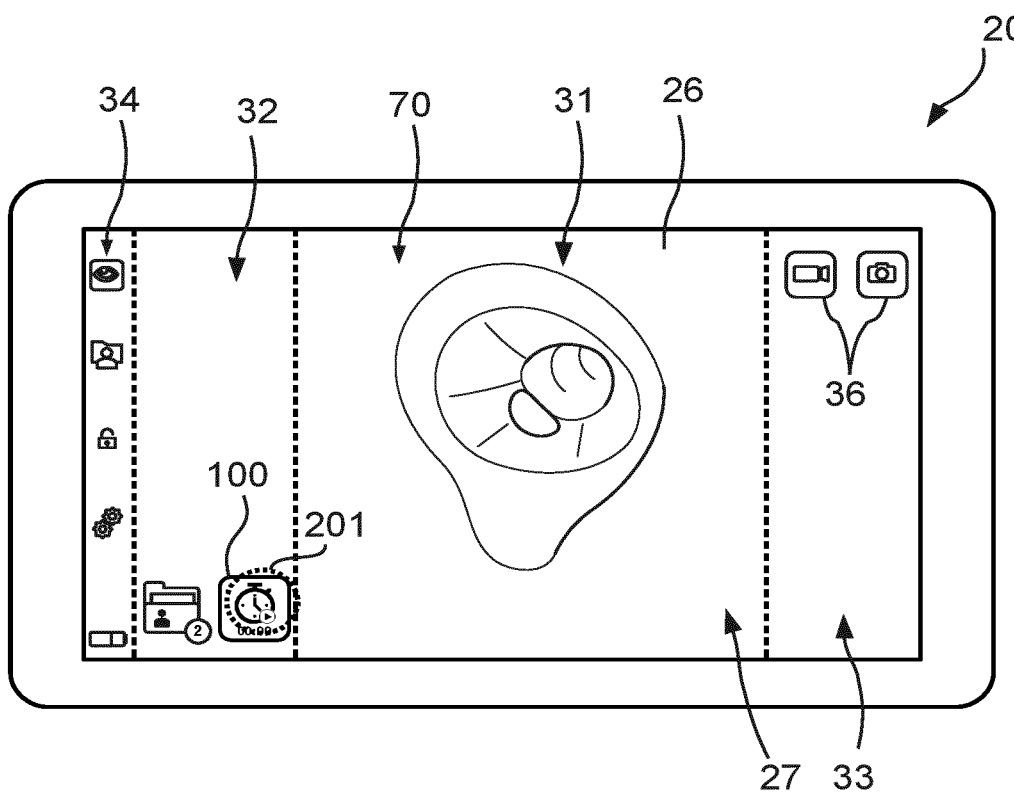
FIGS. 5A-5F schematically illustrates exemplary features of an exemplary graphical user interface, FIGS. 6A-6B schematically illustrates exemplary features of an exemplary graphical user interface, FIGS. 7A-7B schematically illustrates exemplary features of an exemplary graphical user interface, FIGS. 8A-8D schematically illustrates exemplary features of an exemplary graphical user interface, FIG. 9 schematically illustrates exemplary features of an exemplary graphical user interface, FIG. 10 schematically illustrates exemplary features of an exemplary graphical user interface.

Referring to FIG. 5A, the monitor device 20 displays, within the first portion 31 of the graphical user interface, a live representation 70, of the image data received from a coupled medical visualization device. Furthermore, the monitor device 20 displays a stopwatch button 100 within the second portion 32 of the graphical user interface 27.

The stopwatch button 110 is displayed in a first visual mode. The first visual mode may indicate that a time of the stopwatch is not currently active, i.e. has not yet been started or has been paused. The first visual mode includes a play icon, e.g. indicating that once the user taps the button the time will start) and may be shown in a first color, e.g. white.

The monitor device, while displaying the live representation 70 of the image data, is adapted to detect a first user input 201 corresponding to selection of the stopwatch button 100. The first user input may be a touch input on the display 26, which may be a touch sensitive display. However, as described above, the medical visualization device may comprise one or more buttons 18 operable to receive button inputs (see FIG. 1). Thus, alternatively or additionally, a first button signal indicative of a first button input of the one or more buttons 18 may be equivalent to the first user input 201 as described here.

In response to detection of the first user input 201 the monitor device activates a time of a stopwatch. Activation of the time of the stopwatch may in some circumstances be resumption of an earlier stated time, which has been deactivated, such as paused, or it may, as illustrated in the present example, be start of a new time, i.e. starting from 00:00.

Figure 5B:
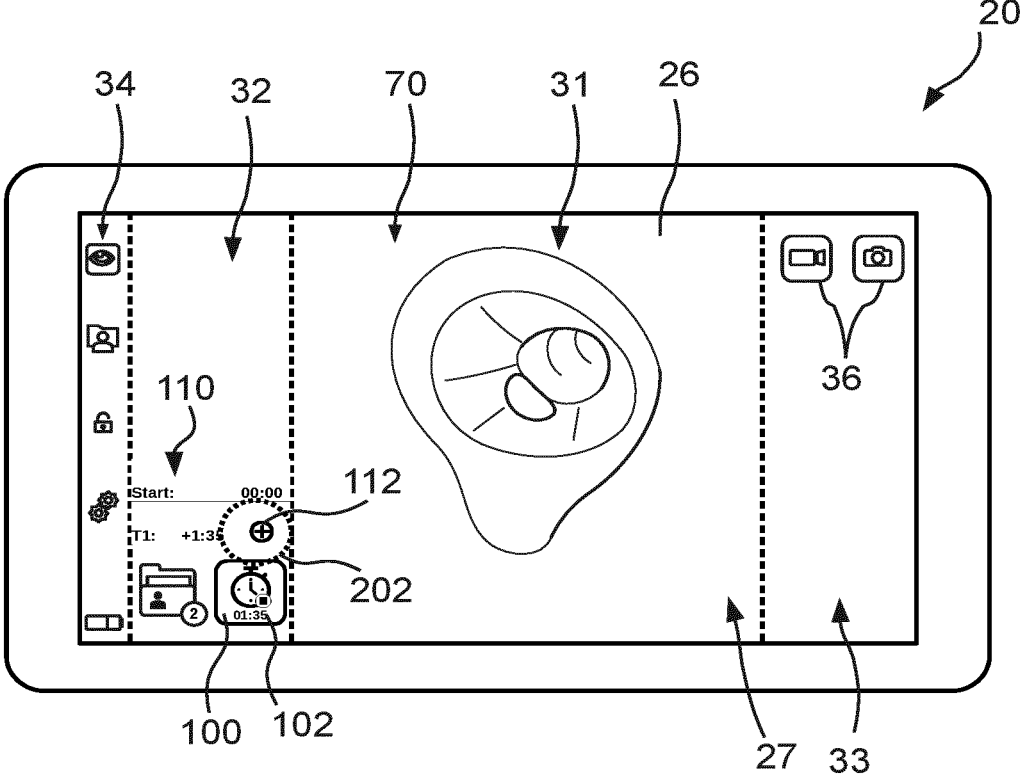

As illustrated in FIG. 5B, in response to detection of the first user input 201 the monitor device 20 updates the stopwatch button 100 to be in a second visual mode. The second visual mode may indicate that the time of the stopwatch is currently active. The second visual mode includes a stop icon, e.g. indicating that once the user taps the button the time will start, and may be shown in a second color, different from the first color, e.g. green.

The stopwatch button 100 comprises a time indicator 102 visually indicating the time of the stopwatch. While the time of the stopwatch is active, the monitor device 20 is adapted to recurrently update the time indicator to indicate the time of the stopwatch. This additionally signals to the user that the stopwatch is active.

Also, in response to detection of the first user input 201, the monitor device, as illustrated in FIG. 5B, displays a timestamp table 110 within the graphical user interface 27. The timestamp table 110 comprises an add timestamp button 112.

Figure 5C:
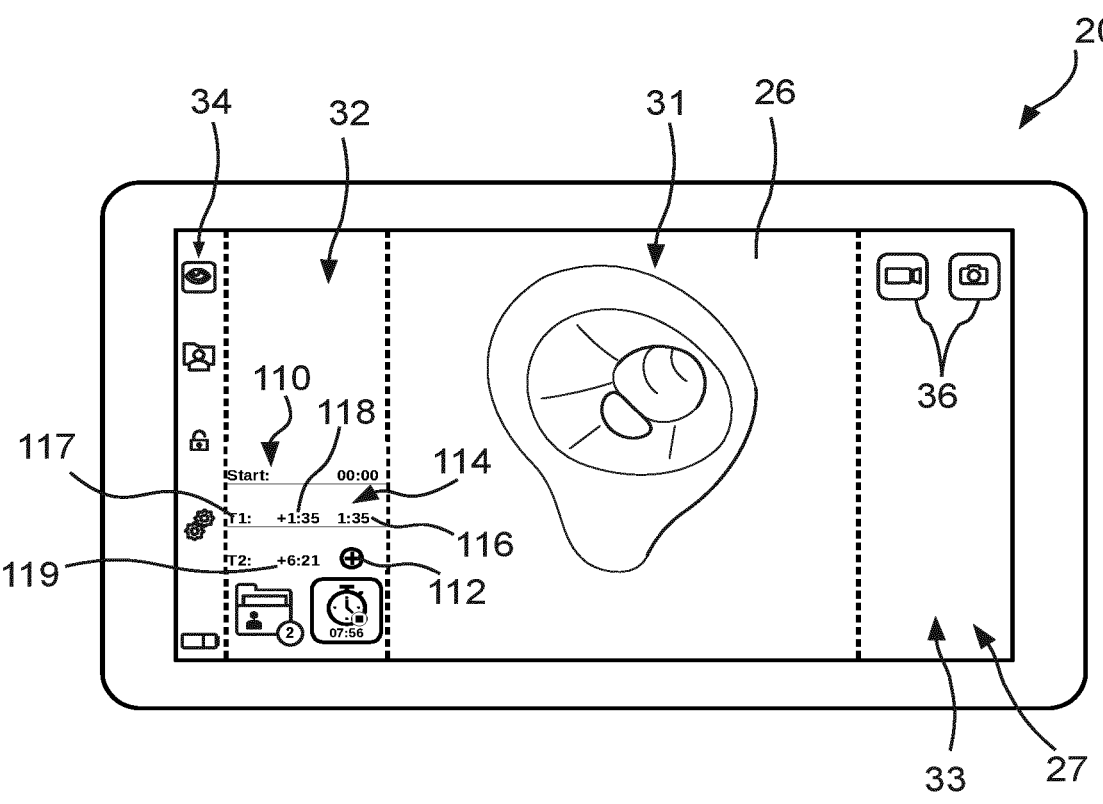

The monitor device 20 is adapted to detect a second user input 202 corresponding to selection of the add timestamp button 112. In response to detection of the second user input 202 the monitor device stores a timestamp comprising a timestamp value corresponding to the time of the stopwatch when detecting the second user input 202. Furthermore, as illustrated in FIG. 5C, the monitor device 20 displays a new timestamp entry 114 in the timestamp table 110, wherein the timestamp entry 114 comprises the respective timestamp value 116 corresponding to the time of the stopwatch when detecting the second user input 202.

The second user input 202 may be a touch input on the display 26, which may be a touch sensitive display. However, as described above, the medical visualization device may comprise one or more buttons 18 operable to receive button inputs (see FIG. 1). Thus, alternatively or additionally, a second button signal indicative of a second button input of the one or more buttons 18 may be equivalent to the second user input 202 as described here.

A timestamp comprises a timestamp name 117. The timestamp entry 114 in the timestamp table 110 comprises the timestamp name 117. The timestamp entry 114 in the timestamp table 110 also comprises a difference value 118 corresponding to a time difference between the timestamp value 116 and a preceding timestamp value of an immediately preceding timestamp entry. In the illustrated example, since the immediately preceding timestamp entry is the start of the stopwatch, the difference value 118 is the same as the timestamp value 116.

The timestamp table 110 comprises an indication of elapsed time 119 since a newest timestamp value. This indication informs the user of the time since the last saved timestamp. While the time of the stopwatch is active, the monitor device 20 may be adapted to recurrently update indication of elapsed time 119 since the newest timestamp value.

The monitor device 20 is adapted to detect additional second user inputs corresponding to selection of the add timestamp button 112. In response to detection of each of the second user inputs corresponding to selection of the add timestamp button 112 the monitor device stores a new timestamp comprising a timestamp value corresponding to the respective time of the stopwatch when detecting the respective second user input.

Figure 5D:
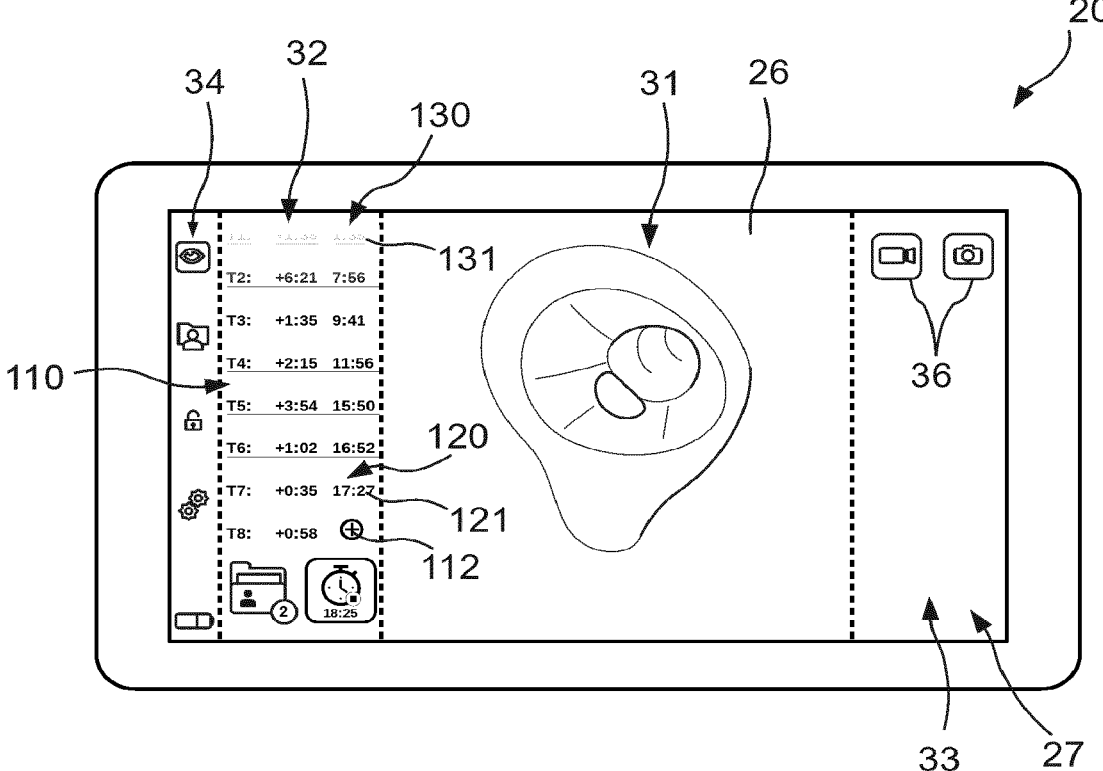

As illustrated in FIG. 5D, the timestamp table 110 comprises a plurality of timestamp entries, e.g. following additional user inputs corresponding to selection of the add timestamp button 112. The plurality of timestamp entries includes a first timestamp entry 120 and a second timestamp entry 130. The first timestamp entry 120 comprises a first timestamp value 121. The second timestamp entry 130 comprises a second timestamp value 131 being before the first timestamp value 121. The second timestamp entry 130 is displayed above the first timestamp entry 120 in the timestamp table 110.

Figure 5E:
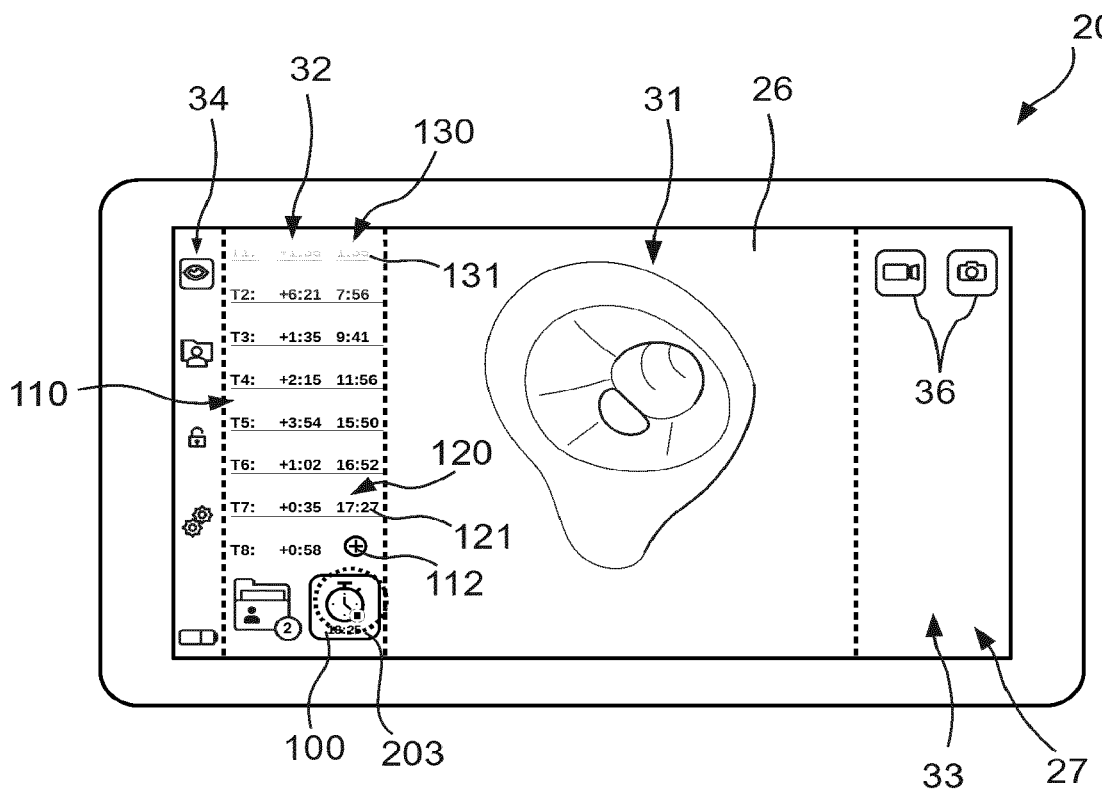

The number of the plurality of timestamp entries in the timestamp table 110, may, as illustrated in FIG. 5D, be more than a threshold number of timestamp entries to display in the second portion 32 of the graphical user interface 27. For example, the threshold number of timestamp entries may be based on the first length L1 of the display 26 in the first direction x1 (see FIG. 2). In the illustrated example, the threshold number of timestamp entries are six. To indicate to the user, that there are more timestamp entries than can be displayed, the second timestamp entry 130 is displayed with fading visibility from bottom to top of the second timestamp entry 130. In some examples, the user may scroll the list by swiping up/down in the second portion 32 of the graphical user interface 27. As illustrated in FIG. 5E, which may follow the illustrated situation of FIG. 5D, while the time of the stopwatch is active, the monitor device 20 is adapted to detect a third user input 203 corresponding to selection of the stopwatch button 100. In response to detection of the third user input 203 the monitor device 20 deactivates the time of the stopwatch.

The third user input 203 may be a touch input on the display 26, which may be a touch sensitive display. However, as described above, the medical visualization device may comprise one or more buttons 18 operable to receive button inputs (see FIG. 1). Thus, alternatively or additionally, a third button signal indicative of a third button input of the one or more buttons 18 may be equivalent to the third user input 203 as described here.

Figure 5F:
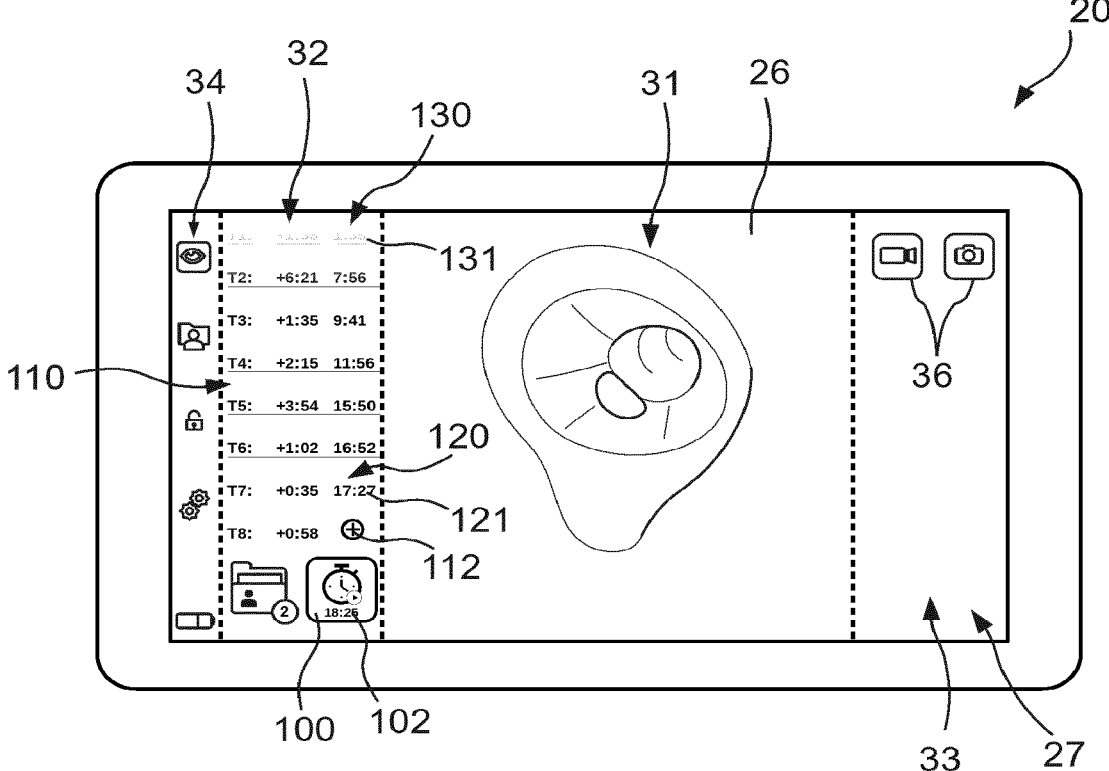

As illustrated in FIG. 5F, also in response to detection of the third user input 203 the monitor device 20 updates the stopwatch button 100 to be in the first visual mode, as described in relation to FIG. 5A. Furthermore, the time indicator 102 of the stopwatch button 100 indicates the time of the stopwatch, i.e. the elapsed time. This additionally signals to the user that the stopwatch is deactivated, as the time indicator is static.

The user may again activate the time of the stopwatch by again selecting the stopwatch button 100, and the monitor device will activate the time of the stopwatch, as explained in relation to FIG. 5A.

Figure 6A:
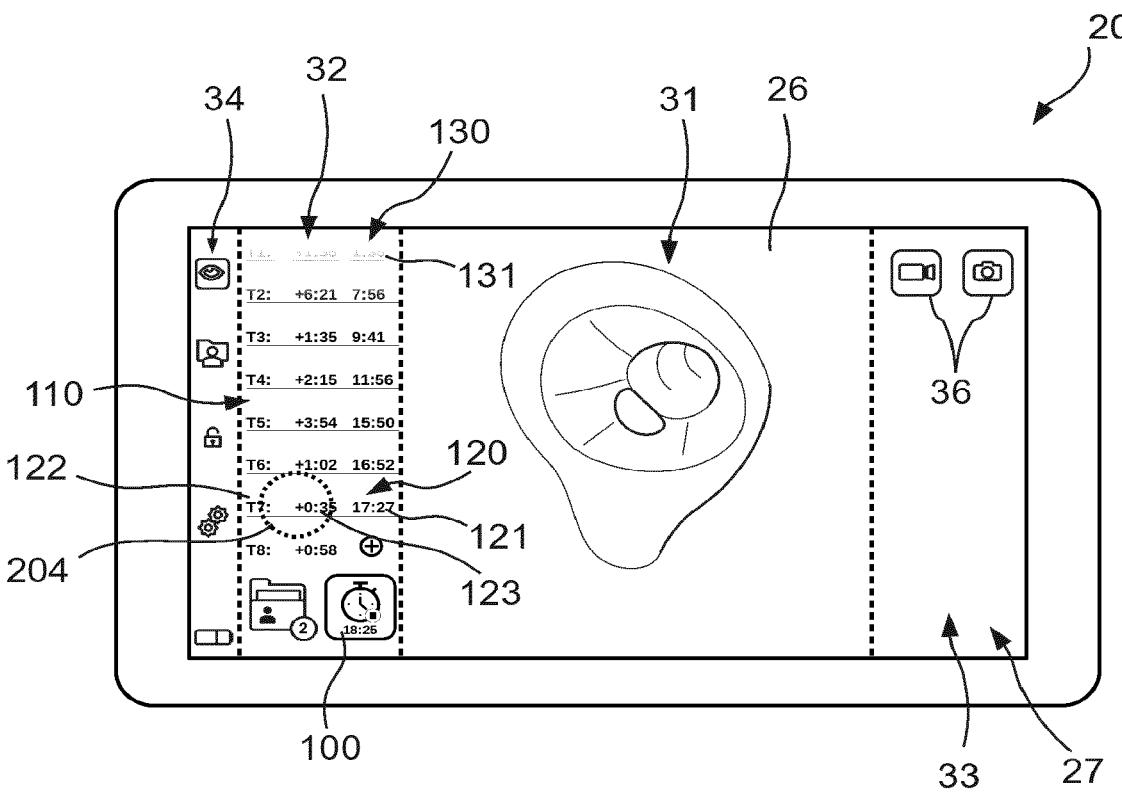

FIG. 6A schematically illustrates further exemplary features of the graphical user interface 27, such as the graphical user interface 27 as described in relation to FIGS. 5A-5F. Particularly, FIG. 6A illustrates an example of the graphical user interface 27 like the one of FIGS. 5D, 5E of 5F.

As previously described, each timestamp may comprise a timestamp name and/or a difference value. For example, the first timestamp entry 120 in the timestamp table 110 comprises a first timestamp name 122 and a first difference value 123 corresponding to a time difference between the first timestamp value 121 and a preceding timestamp value of an immediately preceding timestamp entry.

Figure 6B:
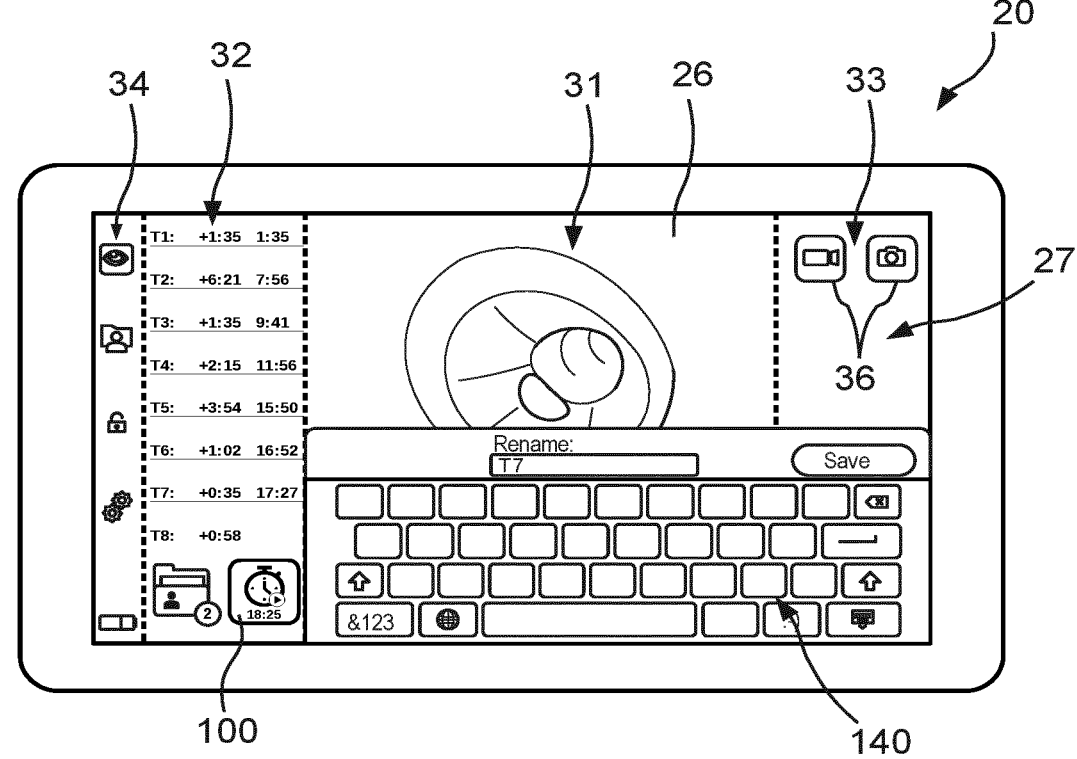

The monitor device 20 is adapted to detect a fourth user input 204 corresponding to selection of the first timestamp entry 120 in the timestamp table 110. In response to detection of the fourth user input 204 the monitor device 20 opens a dialogue 140 enabling editing of the first timestamp name 122. In FIG. 6B, the dialogue 140 is displayed as a soft-keyboard displayed in the first and third portion of the graphical user interface 27.

In another example, the user input 204 may activate a drop-down menu with a list of predefined names to choose from for the timestamp. The predefined names may relate to the anatomy to be examined with the type of medical visualization device used. For example, if using a medical visualization device for performing a procedure in the colon, the predefined names may include landmarks associated with the colon. In another example, if using a medical visualization device for performing a procedure in the lungs, the predefined names may include landmarks associated with the lungs.

The drop-down menu may be configured so that one or more of the predefined names of the list of predefined names, e.g. being anatomical identification names, may be chosen only for one timestamp. For example, such that only one timestamp can be named "cecum" during a colonoscopy procedure. The drop-down menu may be configured so that others of the predefined names of the list of predefined names, e.g. describing special landmarks in the particular anatomy and objects of special interests, may be chosen several times. For example, such that several timestamps can be named "poly" in a colonoscopy procedure. In case of several timestamps being labelled with the same name, they may be provided with a increasing numeral.

Figure 7A:
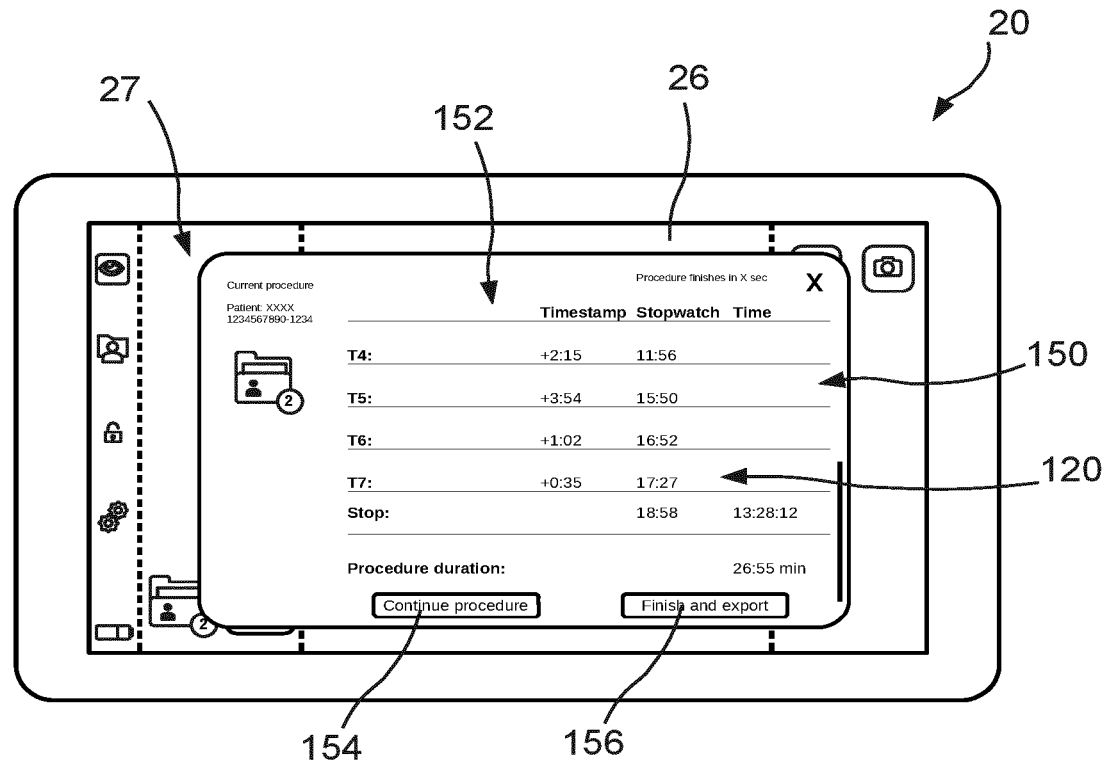
Figure 7B:
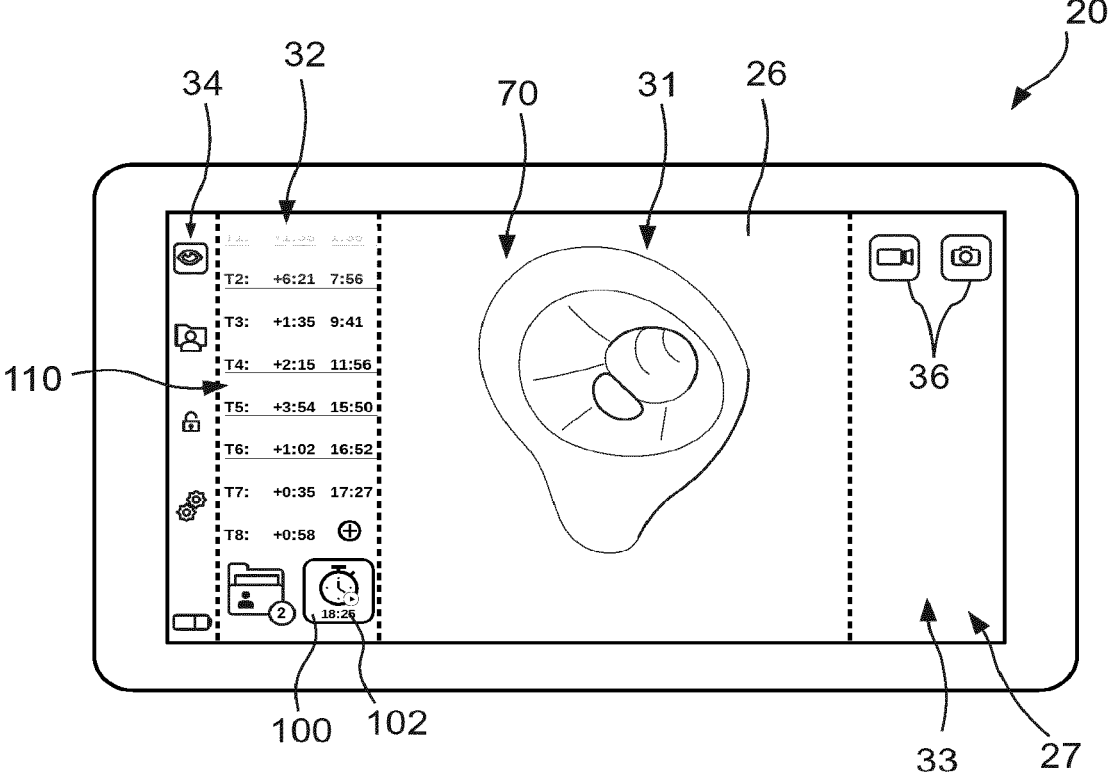

FIGS. 7A-7B schematically illustrates further exemplary features of a graphical user interface 27, such as the graphical user interface 27 as described in relation to FIGS. 5A-5F.

The operator may disconnect the medical visualization device from the monitor device, e.g. by unplugging the device connector 16 from the connection port 40 (cf. FIG. 3). For example, the operator may disconnect the medical visualization device in the situation as illustrated in FIG. 5F.

In response to disconnection of the medical visualization device from the monitor device 20, the monitor device 20 displays a procedure overview 150, as illustrated in FIG. 7A, comprising a second timestamp table 152. The second timestamp table 152 comprises an overview of the time-stamps stored during the procedure. Particularly, the second timestamp table 152 comprises the first timestamp entry 120 and the other timestamp entries of the timestamp table 110, e.g. of FIG. 5F.

After disconnection of the medical visualization device, the operator may reconnect the medical visualization device. For example, the medical visualization device might have been disconnected unintentionally.

In response to reconnection of the medical visualization device to the monitor device the monitor device hides the procedure overview 150, as illustrated in FIG. 7B, and displays the live representation 70 of the image data from the medical visualization device within the first portion 31 of the graphical user interface 27. Also, the monitor device 20 displays the stopwatch button 100 within the second portion 32 of the graphical user interface 27.

In accordance with the medical visualization device being reconnected within a threshold amount of time after disconnection of the medical visualization device, e.g. within 60 seconds of disconnection, the time of the stopwatch is continued. Hence, in response to detection of a user input corresponding to selection of the stopwatch button 100, the time of the stopwatch is deactivated or resumed. The time of the stopwatch may be deactivated in case it is active or may be resumed if it was deactivated prior to disconnection of the medical visualization device.

In the example, as illustrated in FIG. 7B, the medical visualization device has been inserted within the threshold amount of time after disconnection, as evident from the timestamp table 110 and the time indicator 102 of the stopwatch button 100 showing the same time as in FIG. 5F, i.e. before disconnecting the medical visualization device.

Conversely, in accordance with the medical visualization device being reconnected after the threshold amount of time after disconnection of the medical visualization device, e.g. after 60 seconds of disconnection, the time of the previous stopwatch is stored in memory for later retrieval, and a new time of a new stopwatch is initiated. Hence, in response to detection of the fifth user input corresponding to selection of the stopwatch button 100, the monitor device 20 activates a new time of a new stopwatch. This will amount to the situation as illustrated in FIG. 5A/5B.

The procedure overview 150, as illustrated in FIG. 7A, comprises a continue button 154. In accordance with connection of a new medical visualization device to the monitor device 20, the monitor device is adapted to detect a user input corresponding to selection of the continue button 154. In response to detection of the user input corresponding to selection of the continue button 154, the monitor device 20 hides the procedure overview 150, e.g. as illustrated in FIG. 7B, and displays the live representation 70 of the image data from the new medical visualization device within the first portion 31 of the graphical user interface 27. Also, the monitor device 20 displays the stopwatch button 100 within the second portion 32 of the graphical user interface 27.

In accordance with the detection of the user input corresponding to selection of the continue button 154, the time of the stopwatch is continued (like if the same device had been reconnected within the threshold amount of time). Hence, in response to detection of a user input corresponding to selection of the stopwatch button 100, the time of the stopwatch is deactivated or resumed. The time of the stop-watch may be deactivated in case it is active or may be resumed if it was deactivated prior to disconnection of the medical visualization device.

In some examples, the continue button 154 may also be selectable in accordance with reconnection of the previous medical visualization device (e.g. the medical visualization device having previously been disconnected). To allow the user to continue the procedure and the present stopwatch with the same visualization device, even if it is reconnected after the threshold amount of time.

The procedure overview 150, as illustrated in FIG. 7A, further comprises an export button 156 for the operator to export the stored timestamp (and optionally any stored images/videos), e.g. to an external memory. As illustrated, the export button 156 may be a combined export and finish button.

FIGS. 8A-8D schematically illustrates further exemplary features of a graphical user interface 27, such as the graphical user interface 27 as described in relation to FIGS. 5A-5F.

Figure 8A:
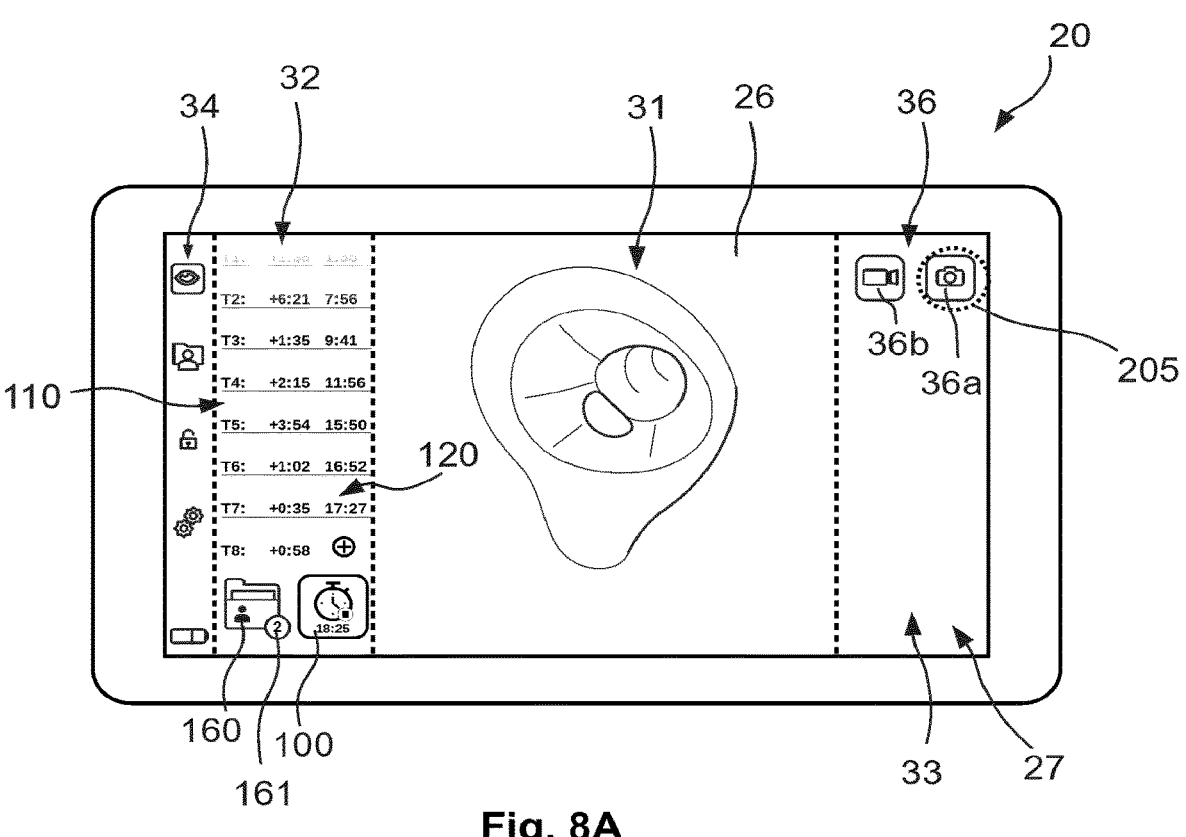

In FIG. 8A, the monitor device displays a timestamp table 110 comprising at least a first timestamp entry 120. For example, the situation of FIG. 8A may amount to the situation as illustrated in FIG. 5D.

As also described with respect to FIG. 3, the monitor device 20 displays one or more actionable items 36 within the third portion 33 of the graphical user interface 27. The actionable items 36 may comprise an image capture button 36a and/or a video capture button 36b.

Furthermore, the monitor device 20 displays a folder icon 160 within the second portion 32 of the graphical user interface 27. In other examples, the folder icon 160 may be displayed in other portions of the graphical user interface 27. The folder icon 160 comprises a visual representation 161 of a count of stored files, e.g. stored during the procedure session.

To capture an image corresponding to the presently shown live representation 70, e.g. corresponding to the image data received from the image sensor, the user may tap the image capture button 36a, e.g. as indicated by user input 205. In response to the user input 205 corresponding to selection of the image capture button 36a, the monitor device 20 stores an image data file, as further explained in relation to FIG. 3. The monitor device 20 may associate the stored image file with a procedure session. For example, the monitor device 20 may store the image file in a folder corresponding to the procedure session. The procedure session may be corresponding to the medical visualization device, e.g. a new procedure session may be opened when coupling a new medical visualization device.

The user input 205 corresponding to selection the image capture button 36a may be a touch input on the display 26, which may be a touch sensitive display. However, as described above, the medical visualization device may comprise one or more buttons 18 operable to receive button inputs (see FIG. 1). Thus, alternatively or additionally, a first button signal indicative of a button input of the one or more buttons 18 may be equivalent to the user input 205 as described here.

Figure 8B:
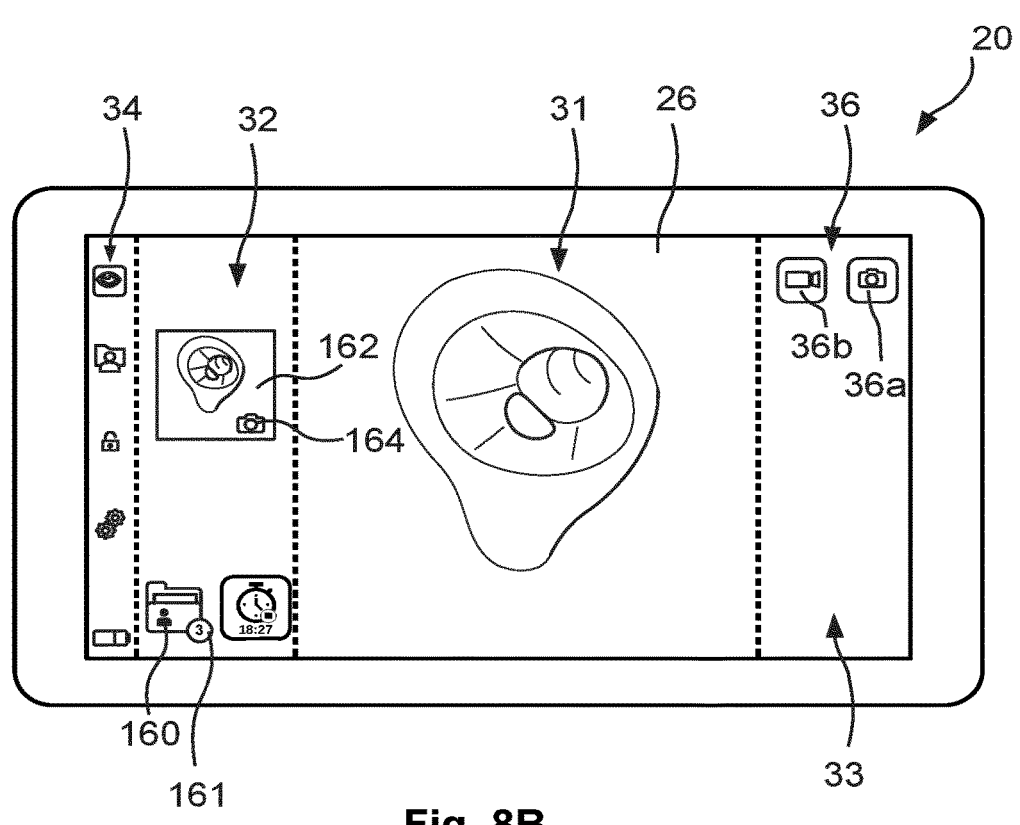

Furthermore, as illustrated in FIG. 8B, the monitor device 20, in response to detection of the user input 205, displays within the second portion 32 of the graphical user interface 27, a representation 162 of a still image corresponding to the stored image file. Thereby, the operator is notified that the monitor device 20 has stored an image, and the operator is further provided with an example of the stored image, e.g. to allow the operator to quickly confirm that the image does show what he/she intended to show. Furthermore, the representation 162 is provided with an icon 164 indicating that the representation 162 correspond to a still image. In case the operator had captured a video recording, the icon 164 would be indicative of a video recording.

When displaying the representation 162 of the still image corresponding to the stored image file, the timestamp table 110 may be hidden. Hence, in response to detection of the user input 205, the monitor device may hide display of the timestamp table 110.

Figures 8C, 8D:
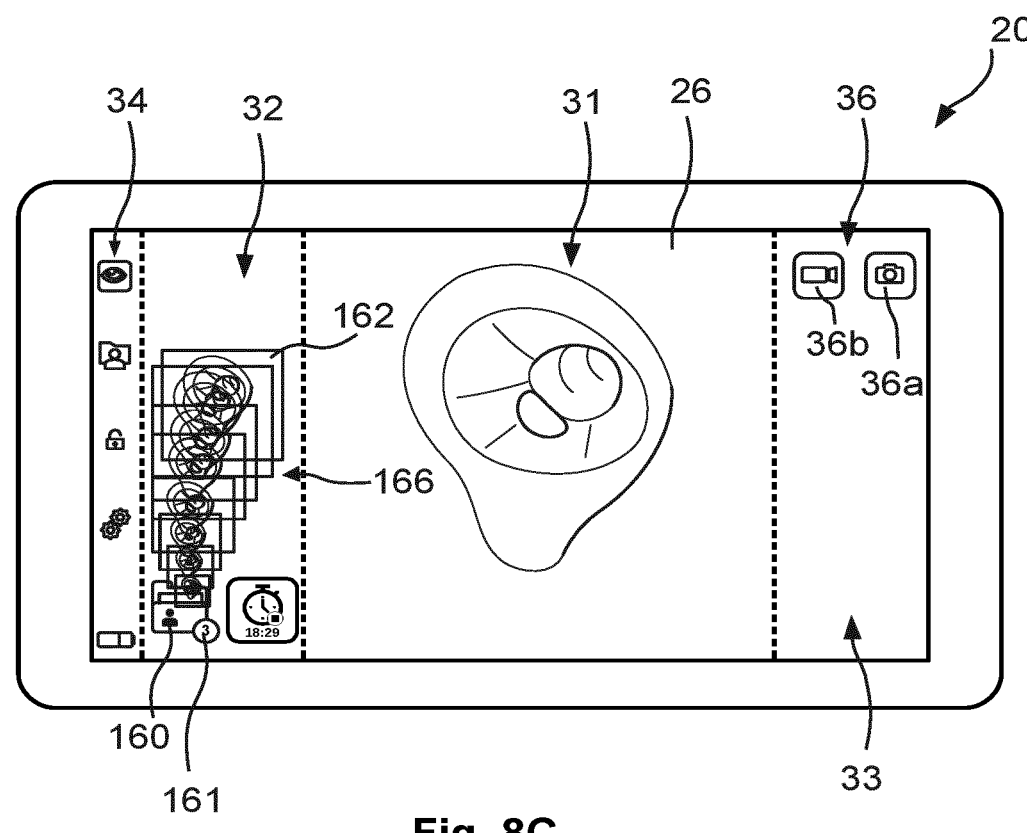

As shown in FIG. 8C, after a predetermined delay after detection of the user input 205 corresponding to selection of the image capture button 36a, the monitor device 20 displays an animation 166 of transitioning the representation 162 to the folder icon 160. The predetermined delay may be between 1-5 seconds, such as between 1.5-3 seconds, such as 1.5 seconds or such as 2 seconds. Thus, the operator is visually notified that the captured image is stored and is placed in the folder represented by the folder icon 160. The animation 166 may have a duration between 100-1500 ms, such as between 300-1000 ms, such as between 300-600 ms, such as 400 ms or 500 ms.

Furthermore, also in response to detection of the user input 205 (cf. FIGS. 8A-8B), the display of the visual representation 161 of the count of stored files stored during the procedure session is updated by increasing the count of stored files. Alternatively, the display of the visual representation 161 of the count of stored files stored during the procedure session may be updated by increasing the count of stored files after display of the animation 166, e.g. in the transition between FIG. 8B and FIG. 8C.

After displaying the animation 166 of transitioning the representation 162 to the folder icon 160, the timestamp table 110 is again displayed in the second portion 32 of the graphical user interface 27, as illustrated in FIG. 8D.

In some examples, the the representation 162 of the still image corresponding to the stored image file and/or animation 166 of transitioning the representation 162 to the folder icon 160, may be overlayed on the timestamp table 110, i.e. the timestamp table may, in some examples, remain at least partly visible while displaying the representation 162 of the still image corresponding to the stored image file and/or the animation 166 of transitioning the representation 162 to the folder icon 160.

While FIGS. 8A-8D explain examples of the behavior related to capturing still images, it will be appreciated that the example may similarly apply had the operator provided the user input 205 to the video capture button 36b.

Figure 9:
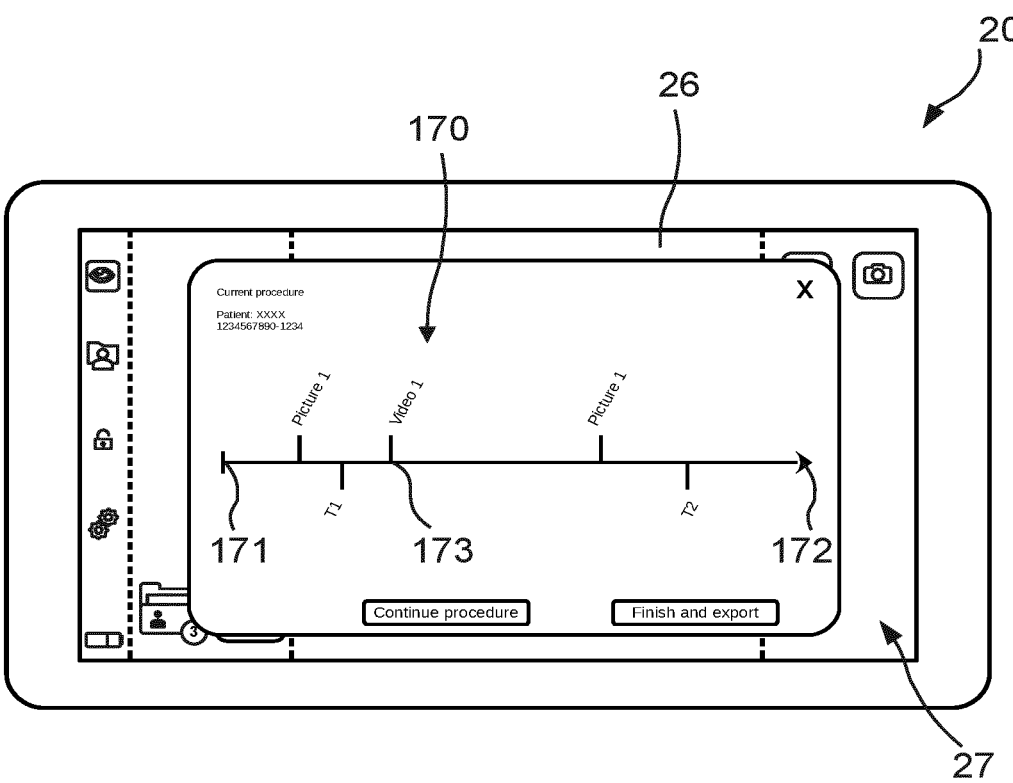

FIG. 9 schematically illustrates further exemplary features of a graphical user interface 27, such as the graphical user interface 27 as described in relation to FIGS. 8A-8D. Particularly, FIG. 9 illustrates an example, where the monitor device 20 displays a timeline 170 indicative of the chronology of the different timestamps and/or images/videos captured. The timeline 170 may be displayed as a dialogue, e.g. after finishing the procedure, e.g. after decoupling of the medical visualization device has been detected. For example, the timeline 170 may be displayed following a procedure overview as illustrated in FIG. 7A, and/or instead of the procedure overview as illustrated in FIG. 7A.

The timeline 170 extends from a first position 171 to a second position 172 and comprising one or more marks 173 between the first position 171 and the second position 172. Each or the one or more marks 173 is indicative of a timestamp or a captured image or a captured video. In the timeline 170 the one or more marks 173 are chronologically ordered along the timeline. Thus, the operator can get a chronological overview of the stored images, videos, and timestamps during the course of the procedure.

Figure 10:
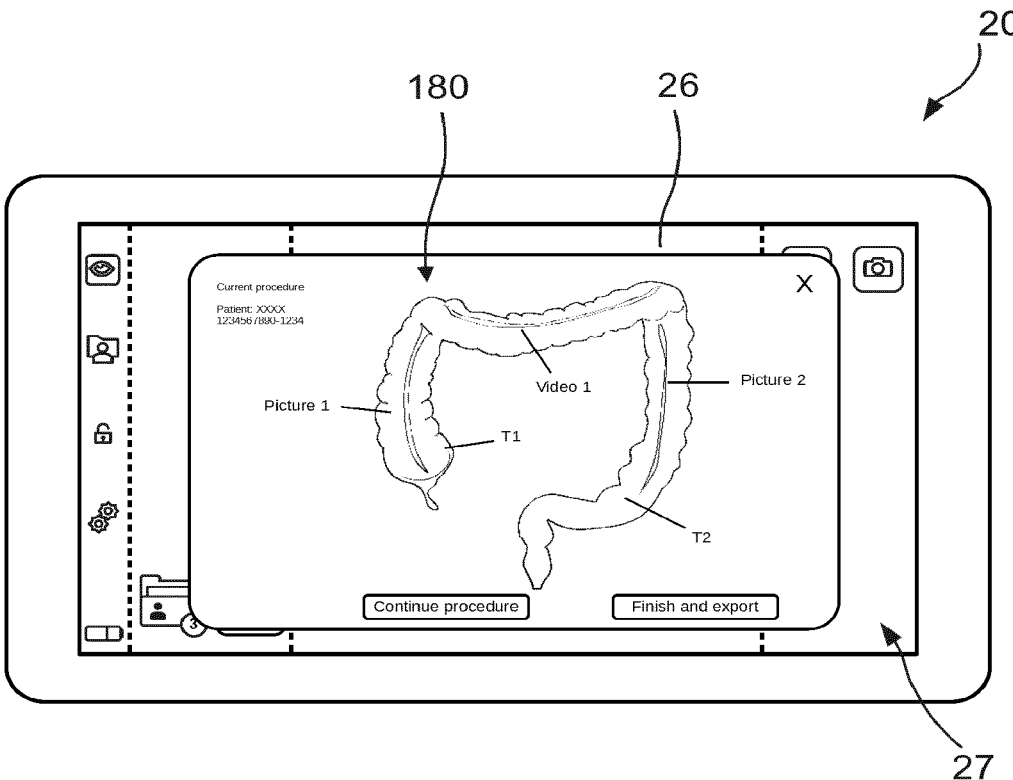

FIG. 10 schematically illustrates further exemplary features of a graphical user interface 27, such as the graphical user interface 27 as described in relation to FIGS. 8A-8D. Particularly, FIG. 10 illustrates an example, where the monitor device 20 displays an anatomical map 180 indicative of the positions within the anatomy (in the present example a colon) of the different timestamps and/or images/videos captured. The anatomical map 180 may be displayed as a dialogue, e.g. after finishing the procedure, e.g. after decoupling of the medical visualization device has been detected. For example, the anatomical map 180 may be displayed following a procedure overview as illustrated in FIG. 7A, and/or instead of the procedure overview as illustrated in FIG. 7A. The anatomical map 180 may be displayed following or before the timeline 170 as illustrated in FIG. 9. For example, the user may choose to have the timestamps and/or images/videos captured shown in chronological order, as provided by the timeline 170, and/or in positional order, as provided by the anatomical map 180.

The anatomical map may be provided based on sensor systems able to sense the position of the image sensor of the medical visualization device. Such sensor systems may, for example, be based on an external array of sensors able to detect the spatial position of the image sensor of the medical visualization device.

The anatomy shown in the anatomical map 180, which in the illustrated example is a representation of a colon, may be based on the type and/or model of the medical visualization device. For example, a representation of a bronchial tree may be displayed when the medical visualization device is of a type intended for investigating the lungs of a patient, and/or a representation of a urinary system may be displayed when the medical visualization device is of a type intended for investigating the urinary system of a patient.

The disclosure has been described with reference to a preferred embodiment. However, the scope of the invention is not limited to the illustrated embodiment, and alterations and modifications can be carried out without deviating from the scope of the invention.

Throughout the description, the use of the terms "first", "second", "third", "fourth", "primary", "secondary", "tertiary" etc. does not imply any particular order or importance but are included to identify individual elements. Furthermore, the labelling of a first element does not imply the presence of a second element and vice versa.

LIST OF REFERENCES 2 medical visualization system
4 visualization device
6 handle
7 control button
8 elongated flexible member
9 distal part
10 distal end of elongated flexible member
12 image sensor
14 device cable
16 device connector
20 monitor device
21 first housing side
22 second housing side
23 third housing side
24 fourth housing side
25 first housing
26 touch sensitive display
27 graphical user interface
31 first portion
32 second portion
33 third portion
34 fourth portion
36 actionable item(s)
37 first image direction
38 second image direction
40 connection port(s)
42 actionable menu item(s)
50 battery indicator
60 processing unit
61 power supply
61a battery
61b power connection
62 memory
64 orientation sensor
66 input/output
68 microphone
70 live representation of image data
100 stopwatch button
102 time indicator
110 timestamp table
112 add timestamp button 114, 120, 130 timestamp entry
116, 121, 131 timestamp value
117, 122 timestamp name
118, 123 difference value
119 elapsed time
140 dialogue
150 procedure overview
152 second timestamp table
154 continue button
156 finish/export button
160 folder icon
161 visual representation of count of stored files
162 representation of stored image/video file
164 icon indicative of image/video
166 animation
170 timeline
171 first position
172 second position
173 mark(s)
201, 202, 203, 204, 205 user input
x1 first direction
x2 second direction
L1 first length
L2 second length

The invention claimed is:

1. A monitor device operable to receive image data from a medical visualization device, the monitor device comprising:

a housing, and a processing unit adapted to receive the image data from the medical visualization device and cause a display to display a graphical user interface, wherein the monitor device:

displays a live representation of the image data within a first portion of the graphical user interface, and displays a stopwatch button within a second portion of the graphical user interface, the second portion and the first portion being non-overlapping, and wherein the monitor device, while displaying the live representation of the image data, is adapted to detect a first user input corresponding to selection of the stopwatch button, and in response to detection of the first user input the monitor device:

activates a time of a stopwatch, and displays a timestamp table within the graphical user interface, wherein the timestamp table comprises an add timestamp button, and wherein the monitor device is adapted to detect a second user input corresponding to selection of the add timestamp button, and in response to detection of the second user input the monitor device:

stores a first timestamp comprising a first timestamp value corresponding to the time of the stopwatch when detecting the second user input, and displays a first timestamp entry in the timestamp table comprising the first timestamp value.

2. The monitor device of claim 1, wherein, while the time of the stopwatch is active, the monitor device is adapted to detect a third user input corresponding to selection of the stopwatch button, and in response to detection of the third user input the monitor device deactivates the time of the stopwatch.

3. The monitor device of claim 1, wherein the stopwatch button, prior to detection of the first user input, is displayed in a first visual mode, and wherein in response to detection of the first user input the monitor device updates the stopwatch button to be in a second visual mode.

4. The monitor device of claim 3, wherein, in response to detection of the third user input, the monitor device updates the stopwatch button to be in the first visual mode.

5. The monitor device of claim 1, wherein the stopwatch button comprises a time indicator visually indicating the time of the stopwatch, and while the time of the stopwatch is active, the monitor device is adapted to recurrently update the time indicator to indicate the time of the stopwatch.

6. The monitor device of claim 1, wherein the first timestamp comprises a first timestamp name, and wherein the first timestamp entry in the timestamp table comprises the first timestamp name.

7. The monitor device of claim 6, wherein the monitor device is adapted to detect a fourth user input corresponding to selection of the first timestamp entry in the timestamp table, and in response to detection of the fourth user input, the monitor device opens a dialogue enabling editing of the first timestamp name.

8. The monitor device of claim 1, wherein the first timestamp entry in the timestamp table comprises a first difference value corresponding to a time difference between the first timestamp value and a preceding timestamp value of an immediately preceding timestamp entry.

9. The monitor device of claim 1, wherein the timestamp table comprises an indication of elapsed time since a newest timestamp value.

10. The monitor device of claim 1, wherein after detection of the second user input, the timestamp table comprises a plurality of timestamp entries including the first timestamp entry and a second timestamp entry, the second timestamp entry comprising a second timestamp value being before the first timestamp value, and wherein the second timestamp entry is displayed above the first timestamp entry in the timestamp table.

11. The monitor device of claim 10, wherein the number of the plurality of timestamp entries are more than a threshold number of timestamp entries to display in the second portion of the graphical user interface, and wherein the second timestamp entry is displayed with fading visibility from bottom to top of the second timestamp entry, wherein optionally the threshold number of timestamp entries is based on a first length of the display in a first direction.

12. The monitor device of claim 1, wherein in response to disconnection of the medical visualization device from the monitor device, the monitor device displays a procedure overview comprising a second timestamp table comprising the first timestamp entry.

13. The monitor device of claim 12, wherein in response to reconnection of the medical visualization device to the monitor device, the monitor device:

hides the procedure overview, displays the live representation of the image data within the first portion of the graphical user interface, displays the stopwatch button within the second portion of the graphical user interface, and in accordance with the medical visualization device being reconnected within a threshold amount of time after disconnection of the medical visualization device:

in response to detection of a fifth user input corresponding to selection of the stopwatch button, deactivates or resumes the time of the stopwatch, and in accordance with the medical visualization device being reconnected after the threshold amount of time after disconnection of the medical visualization device:

in response to detection of the fifth user input corresponding to selection of the stopwatch button, activates a new time of a new stopwatch.

14. The monitor device of claim 12, wherein the procedure overview comprises a continue button, and in accordance with connection of a new medical visualization device to the monitor device, the monitor device is adapted to detect a sixth user input corresponding to selection of the continue button, and in response to detection of the sixth user input:

hides the procedure overview, displays the live representation of the image data within the first portion of the graphical user interface, displays the stopwatch button within the second portion of the graphical user interface, and in response to detection of a seventh user input corresponding to selection of the stopwatch button, deactivates or resumes the time of the stopwatch.

15. The monitor device of claim 1, wherein the monitor device displays a timeline extending from a first position to a second position and comprising one or more marks between the first position and the second position, wherein each or the one or more marks is indicative of a timestamp, or a captured image, and wherein the one or more marks are chronologically ordered along the timeline.

16. A medical visualization system comprising the monitor device of claim 1 and the medical visualization device, the medical visualization device comprising:

an image sensor adapted to generate image data indicative of a view from the medical visualization device, and a handle.

17. The medical visualization system of claim 16, wherein the handle comprises one or more buttons operable to receive a first button input and a second button input, and wherein the medical visualization device is operable to transmit a first button signal indicative of the first button input and a second button signal indicative of the second button input to the monitor device, and wherein in response to receipt of the first button signal the monitor device:

activates the time of the stopwatch, and displays the timestamp table, and in response to receipt of the second button signal the monitor device:

stores a primary timestamp comprising a primary timestamp value corresponding to the value of the time of the stopwatch when receiving the second button signal, and displays a primary timestamp entry in the timestamp table comprising the primary timestamp value.

* * * * *